(12) United States Patent
Steege

(10) Patent No.: US 12,053,173 B2
(45) Date of Patent: Aug. 6, 2024

(54) SUTURING SYSTEM

(71) Applicant: Cypris Medical, Inc., Chicago, IL (US)

(72) Inventor: Adam T. C. Steege, Durham, NC (US)

(73) Assignee: Cypris Medical, Inc., Chicago, IL (US)

( * ) Notice: Subject to any disclaimer, the term of this patent is extended or adjusted under 35 U.S.C. 154(b) by 798 days.

(21) Appl. No.: 17/143,388

(22) Filed: Jan. 7, 2021

(65) Prior Publication Data

US 2021/0169470 A1  Jun. 10, 2021

Related U.S. Application Data

(63) Continuation of application No. 15/917,217, filed on Mar. 9, 2018, now Pat. No. 10,898,181.

(60) Provisional application No. 62/473,271, filed on Mar. 17, 2017.

(51) Int. Cl.
*A61B 17/04* (2006.01)
*A61B 17/06* (2006.01)

(52) U.S. Cl.
CPC ...... *A61B 17/0491* (2013.01); *A61B 17/0485* (2013.01); *A61B 17/06061* (2013.01)

(58) Field of Classification Search
CPC ............ A61B 17/0491; A61B 17/0485; A61B 17/06061; A61B 17/0469; A61B 17/0482; A61B 17/0483
See application file for complete search history.

(56) References Cited

U.S. PATENT DOCUMENTS

| | | |
|---|---|---|
| 3,206,217 A | 9/1965 | Shepard et al. |
| 4,210,148 A | 7/1980 | Stivala |
| 4,268,481 A | 5/1981 | Souvaniemi et al. |
| 4,373,530 A | 2/1983 | Kilejian |
| 4,841,888 A | 6/1989 | Mills et al. |
| 4,950,283 A | 8/1990 | Dzubow et al. |
| 5,080,663 A | 1/1992 | Mills et al. |
| 5,507,754 A | 4/1996 | Green et al. |
| 5,525,302 A | 6/1996 | Astle |
| 5,549,617 A | 8/1996 | Green et al. |
| 5,562,686 A | 10/1996 | Sauer et al. |
| 5,766,186 A | 6/1998 | Faraz et al. |
| 5,792,153 A | 8/1998 | Swain et al. |
| 5,792,163 A | 8/1998 | Swain et al. |
| 5,797,927 A | 8/1998 | Yoon |

(Continued)

FOREIGN PATENT DOCUMENTS

| | | |
|---|---|---|
| CN | 206777365 | 12/2017 |
| EP | 0674875 A1 | 10/1995 |

(Continued)

OTHER PUBLICATIONS

Japanese Patent Application No. 2022-176182, Official Action mailed Sep. 26, 2023, 11 pages (with English translation).

(Continued)

*Primary Examiner* — Sarah W Aleman
*Assistant Examiner* — Mikail A Mannan
(74) *Attorney, Agent, or Firm* — James B. Conte; Craig R. Miles; CR MILES P.C.

(57) ABSTRACT

A suturing system including apparatus and methods for disposing stitches in a substrate comprising a thread carrier which inserts a thread in the substrate at a first location and withdraws the thread from the substrate at a second location.

9 Claims, 19 Drawing Sheets

(56) References Cited

U.S. PATENT DOCUMENTS

| | | | |
|---|---|---|---|
| 5,908,426 A | 6/1999 | Pierce | |
| 5,954,057 A | 9/1999 | Li | |
| 5,984,932 A | 11/1999 | Yoon | |
| 6,048,351 A | 4/2000 | Gordon et al. | |
| 6,059,800 A | 5/2000 | Hart et al. | |
| 6,077,276 A | 6/2000 | Kontos | |
| 6,155,989 A | 12/2000 | Collins | |
| 6,346,111 B1 | 2/2002 | Gordon et al. | |
| 6,464,707 B1 | 10/2002 | Bjerken | |
| 6,533,796 B1 | 3/2003 | Sauer et al. | |
| 6,936,054 B2 | 8/2005 | Chu | |
| 6,955,643 B2 | 10/2005 | Gellman et al. | |
| 6,997,931 B2 | 2/2006 | Sauer et al. | |
| 7,033,370 B2 | 4/2006 | Gordon et al. | |
| 7,060,077 B2 | 6/2006 | Gordon et al. | |
| 7,060,079 B2 | 6/2006 | Wulc et al. | |
| 7,063,710 B2 | 6/2006 | Takamoto et al. | |
| 7,175,636 B2 | 2/2007 | Yamamoto et al. | |
| 7,220,266 B2 | 5/2007 | Gambale | |
| 7,399,304 B2 | 7/2008 | Gambale et al. | |
| 7,442,198 B2 | 10/2008 | Gellman et al. | |
| 7,517,356 B2 | 4/2009 | Heinrich | |
| 7,731,727 B2 | 1/2010 | Sauer | |
| 7,763,036 B2 | 7/2010 | Stokes et al. | |
| 7,780,684 B2 | 8/2010 | Wulc et al. | |
| 7,833,236 B2 | 11/2010 | Stokes et al. | |
| 7,846,169 B2 | 12/2010 | Shelton, IV et al. | |
| 7,951,157 B2 | 5/2011 | Gambale | |
| 8,057,386 B2 | 11/2011 | Azonian et al. | |
| 8,075,573 B2 | 12/2011 | Gambale et al. | |
| 8,100,920 B2 | 1/2012 | Gambale et al. | |
| 8,177,794 B2 | 5/2012 | Cabrera et al. | |
| 8,177,797 B2 | 5/2012 | Shimoji et al. | |
| 8,206,284 B2 | 6/2012 | Azonian et al. | |
| 8,226,665 B2 | 7/2012 | Cohen | |
| 8,246,637 B2 | 8/2012 | Viola et al. | |
| 8,257,369 B2 | 9/2012 | Gellman et al. | |
| 8,286,847 B2 | 10/2012 | Taylor | |
| 8,292,886 B2 | 10/2012 | Kerr et al. | |
| 8,292,905 B2 | 10/2012 | Taylor et al. | |
| 8,292,906 B2 | 10/2012 | Taylor et al. | |
| 8,313,509 B2 | 11/2012 | Kostrzewski | |
| 8,337,515 B2 | 12/2012 | Viola et al. | |
| 8,372,090 B2 | 2/2013 | Wingardner et al. | |
| 8,403,837 B2 | 3/2013 | Okoniewski | |
| 8,413,869 B2 | 4/2013 | Heinrich | |
| 8,465,499 B2 | 6/2013 | Onuki et al. | |
| 8,475,453 B2 | 7/2013 | Marczyk et al. | |
| 8,490,851 B2 | 7/2013 | Blier et al. | |
| 8,496,674 B2 | 7/2013 | Cabrera et al. | |
| 8,506,581 B2 | 8/2013 | Wingardner, III et al. | |
| 8,628,545 B2 | 1/2014 | Cabrera et al. | |
| 8,636,752 B2 | 1/2014 | Cabrera et al. | |
| 8,641,729 B2 | 2/2014 | Filipi et al. | |
| 8,721,640 B2 | 5/2014 | Taylor et al. | |
| 8,747,424 B2 | 6/2014 | Taylor et al. | |
| 8,882,785 B2 | 11/2014 | DiCesare et al. | |
| 8,906,041 B2 | 12/2014 | Chu | |
| 8,968,339 B2 | 3/2015 | Malkowski | |
| 8,968,340 B2 | 3/2015 | Chowaniec et al. | |
| 8,968,342 B2 | 3/2015 | Wingardner, III et al. | |
| 9,113,860 B2 | 8/2015 | Viola et al. | |
| 9,149,270 B2 | 10/2015 | Fogel | |
| 9,204,924 B2 | 12/2015 | Marczyk et al. | |
| 9,326,770 B2 | 5/2016 | Shelton, IV et al. | |
| 9,504,465 B2 | 11/2016 | Chu | |
| 10,231,729 B2 | 3/2019 | Sauer | |
| 10,390,818 B2 | 8/2019 | Keyser et al. | |
| 10,631,855 B2 | 4/2020 | Smith | |
| 11,103,236 B2 | 8/2021 | Taylor et al. | |
| 2002/0038125 A1 | 3/2002 | Hamilton | |
| 2002/0119177 A1 | 8/2002 | Bowman et al. | |
| 2003/0208209 A1 | 11/2003 | Gambale et al. | |
| 2004/0015177 A1 | 1/2004 | Chu | |
| 2004/0034371 A1 | 2/2004 | Lehman et al. | |
| 2004/0158125 A1 | 8/2004 | Azoian et al. | |
| 2004/0181238 A1 | 9/2004 | Zarbatany et al. | |
| 2004/0236353 A1 | 11/2004 | Bain et al. | |
| 2005/0251153 A1 | 11/2005 | Sakamoto et al. | |
| 2006/0036232 A1 | 2/2006 | Primavera et al. | |
| 2006/0047289 A1 | 3/2006 | Fogel | |
| 2006/0085016 A1 | 4/2006 | Eremia | |
| 2007/0021736 A1 | 1/2007 | Johnson | |
| 2007/0129735 A1 | 6/2007 | Filipi et al. | |
| 2007/0255296 A1 | 11/2007 | Sauer | |
| 2008/0147096 A1 | 6/2008 | Azonian et al. | |
| 2009/0018580 A1 | 1/2009 | Wulc | |
| 2009/0312775 A1 | 12/2009 | Gilkey | |
| 2010/0016868 A1 | 1/2010 | Kim | |
| 2010/0137888 A1 | 6/2010 | Wulc et al. | |
| 2010/0249498 A1 | 9/2010 | Wingardner et al. | |
| 2011/0082347 A1 | 4/2011 | Okoniewski | |
| 2012/0016383 A1 | 1/2012 | Sauer et al. | |
| 2012/0029536 A1 | 2/2012 | Dicesare et al. | |
| 2012/0215235 A1 | 8/2012 | Fogel | |
| 2013/0035688 A1 | 2/2013 | Kerr et al. | |
| 2013/0172685 A1 | 7/2013 | Okoniewski | |
| 2013/0325058 A1 | 12/2013 | Roorda et al. | |
| 2014/0114309 A1 | 4/2014 | Payne et al. | |
| 2014/0163375 A1 | 6/2014 | Wasielewski | |
| 2014/0371760 A1 | 12/2014 | Menn | |
| 2015/0257751 A1 | 9/2015 | Bachar et al. | |
| 2015/0359531 A1 | 12/2015 | Sauer | |
| 2016/0213228 A1 | 7/2016 | Rohl et al. | |
| 2016/0338691 A1 | 11/2016 | Weber et al. | |
| 2017/0020510 A1* | 1/2017 | Skinlo | A61B 17/0469 |
| 2017/0095363 A1 | 4/2017 | Hiernaux et al. | |
| 2019/0307445 A1 | 10/2019 | Taylor et al. | |

FOREIGN PATENT DOCUMENTS

| | | |
|---|---|---|
| EP | 3 297 540 A1 | 3/2018 |
| EP | 3572005 A2 | 11/2019 |
| JP | 2005-296644 | 10/2005 |
| JP | 2006-512108 | 4/2006 |
| JP | 2011-528949 | 12/2011 |
| WO | 2004/062466 | 7/2004 |
| WO | WO 2006/023975 A2 | 3/2006 |
| WO | WO 2017/075309 A1 | 5/2017 |

OTHER PUBLICATIONS

Japanese Patent Application No. 2022-564747, Official Action mailed Dec. 1, 2023, 10 pages (with English translation).
Israeli Patent Application No. 289477, Official Action dated Jul. 14, 2022, 6 pages.
Covidien. SILS™ Stitch Articulating Suturing Device. Product Sheet, www.covidiet.com, originally downloaded Jan. 6, 2016, 2 pages.
Covidien. V-Loc™ Wound Closure Reload for Use With Endo Stitch™ and SILS™ Stitch Suturing Devices. Product Sheet, www.covidiet.com, originally downloaded Jan. 6, 2016, 28 pages.
Eremia et al. Novel Face-Lift Suspension Suture and Inserting Instrument: Use of Large Anchors Knotted into a Suture with Attached Needle and Inserting Device Allowing for Single Entry Point Placement of Suspension Suture. Preliminary Report of 20 Cases with 6-to 12-Month Follow-Up. Dermatol Surg., Mart 2006, 32(3):335-45.
PCT International Patent Application No. PCT/US07/21449, filed Oct. 5, 2007.
U.S. Appl. No. 60/958,474, filed Jul. 6, 2007.
U.S. Appl. No. 60/923,980, filed Apr. 17, 2007.
U.S. Appl. No. 60/923,804, filed Apr. 16, 2007.
U.S. Appl. No. 60/849,561, filed Oct. 5, 2006.
U.S. Appl. No. 60/849,508, filed Oct. 5, 2006.
U.S. Appl. No. 60/849,562, filed Oct. 5, 2006.
U.S. Appl. No. 62/473,271, filed Mar. 17, 2017.
PCT International Patent Application No. PCT/US18/21942, filed Mar. 12, 2018.
PCT International Patent Application No. PCT/US18/21942; International Search Report and Written Opinion of the International Searching Authority dated May 24, 2018, 13 pages.

(56) References Cited

OTHER PUBLICATIONS

U.S. Appl. No. 15/947,612, filed Apr. 6, 2018.
PCT International Patent Application No. PCT/US18/27173, filed Apr. 11, 2018.
PCT International Patent Application No. PCT/US18/27173; International Search Report and Written Opinion of the International Searching Authority dated Jun. 29, 2018, 8 pages.
PCT International Patent Application No. PCT/US18/37406; International Search Report and Written Opinion of the International Searching Authority dated Sep. 13, 2018, 10 pages.
U.S. Appl. No. 15/917,217, filed Mar. 9, 2018.
U.S. Appl. No. 15/917,217; Office Action mailed Sep. 18, 2019.
U.S. Appl. No. 15/917,217; Office Action mailed Mar. 18, 2020.
U.S. Appl. No. 15/947,612; Office Action mailed Dec. 11, 2019.
U.S. Appl. No. 15/947,612; Office Action mailed Jan. 14, 2020.
U.S. Appl. No. 16/734,121, filed Jan. 3, 2020.
U.S. Appl. No. 15/994,932, Office Action mailed Mar. 4, 2020.
U.S. Appl. No. 15/994,932; Office Action mailed Jul. 21, 2020.
Canadian Patent Application No. 3,096,018, Examination Office Action dated May 18, 2023, 3 pages.
PCT International Patent Application No. PCT/US21/31564, International Search Report and Written Opinion of the International Searching Authority mailed Oct. 27, 2021, 19 pages.
Japanese Patent Application No. 2020-566288, Official Action mailed Feb. 16, 2022, 13 pages (with English translation).
European Patent Application No. 18920964.6, Extended European Search Report dated Jan. 27, 2022, 10 pages.
European Patent Application No. 18913691.4, Extended European search Report dated Feb. 8, 2022, 15 pages.
European Patent Application N. 18913691.4, Supplementary Partial European Search Report mailed Dec. 12, 2021, 15 pages.
Japanese Patent Application No. 2022-176182, Official Action mailed Sep. 22, 2023, 115,954,057 pages (with English translation).
Japanese Patent Application No. 2021-503693, Office Action mailed Jan. 19, 2022, 10 pages (with English translation).
Australian Patent Application No. 2018417948, Examination Report No. 1, dated Apr. 26, 2023, 3 pages.
U.S. Appl. No. 17/315,119, Office Action mailed Oct. 11, 2022.
U.S. Appl. No. 16/734,121, Office Action mailed Feb. 2, 2021.
U.S. Appl. No. 17/315,119, Office Action mailed Oct. 4, 2023.
Boston Scientific. Capio™ SLIM Suture Capturing Device. Website https://www.bostonscientific.com/capio-slim/pdf, originally downloaded Apr. 14, 2021, 4 pages.
Chinese Patent Application No. 201880093578.2, Office Action dated Dec. 26, 2023, 19 pages (with English translation).
U.S. Appl. No. 17/315,119, Office Action dated Oct. 4, 2023.

* cited by examiner

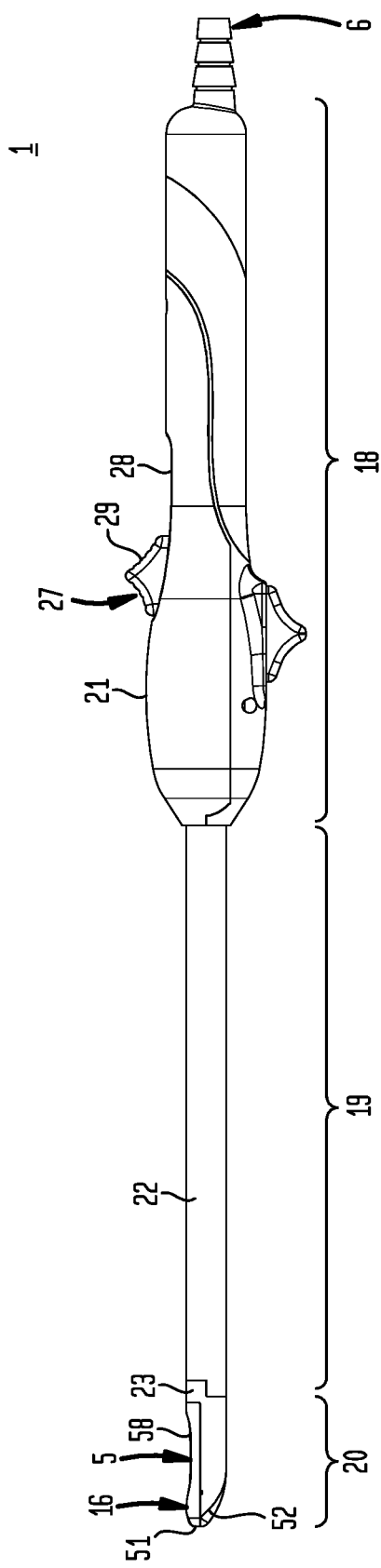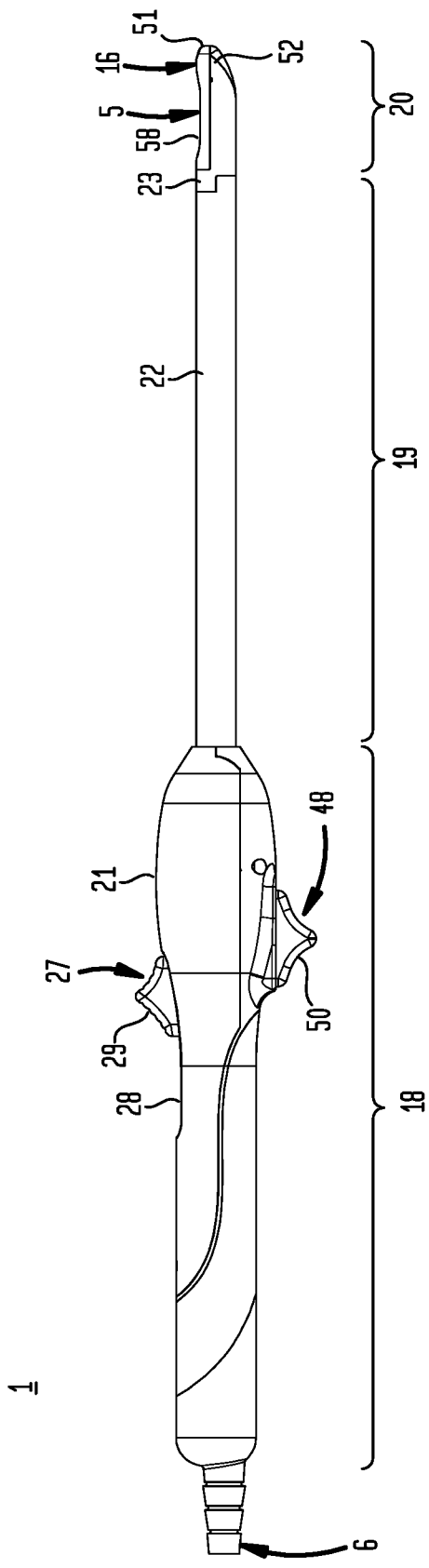

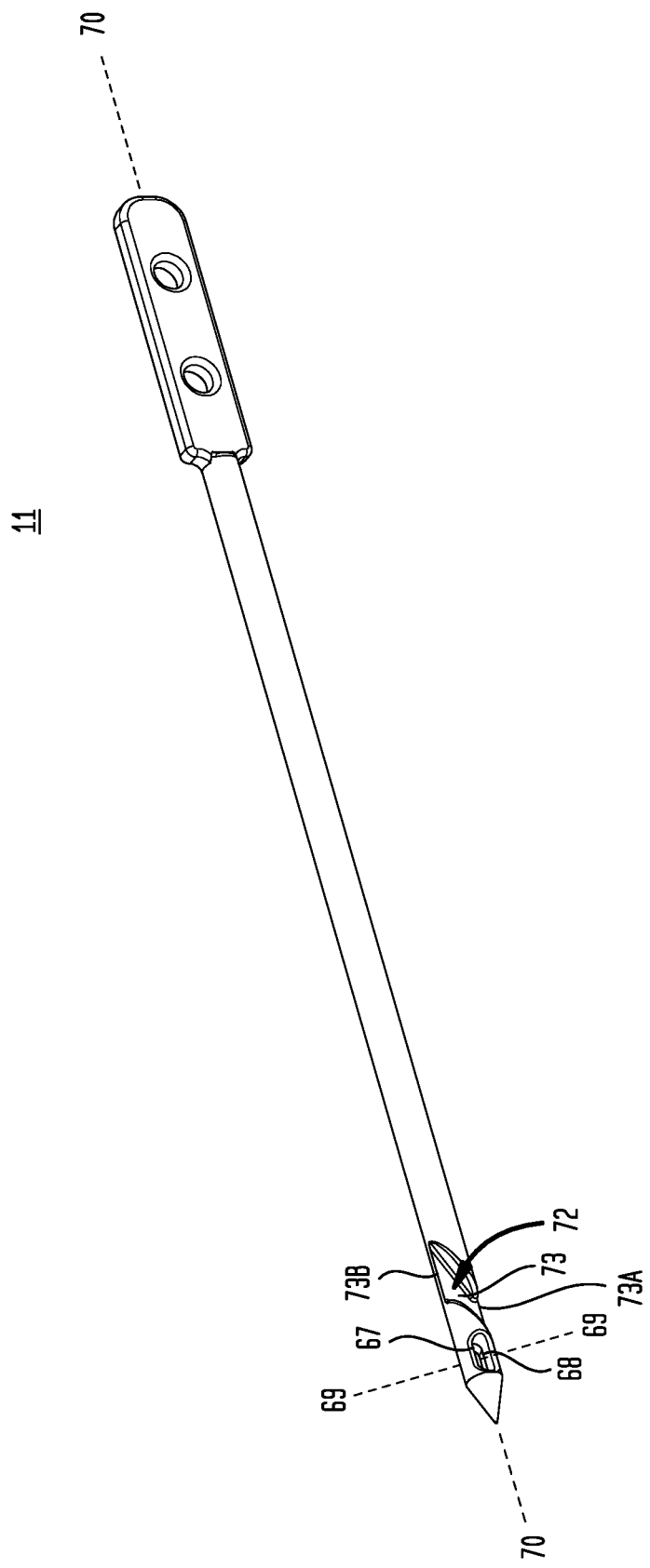

SUTURING SYSTEM

This U.S. patent application is a continuation of U.S. patent application Ser. No. 15/917,217, filed Mar. 9, 2018, now U.S. Pat. No. 10,898,181, issued Jan. 26, 2021, which claims the benefit of U.S. Provisional Patent Application No. 62/473,271, filed Mar. 17, 2017, each hereby incorporated by reference herein.

I. BACKGROUND

A suturing system including apparatus and methods for disposing stitches in a substrate comprising a thread carrier which inserts a thread in the substrate at a first location and withdraws the thread from the substrate at a second location.

II. SUMMARY OF THE INVENTION

A suturing apparatus including one or more of: a housing which maintains in operable relation a valved conduit operable to regulate fluid flow between a substrate capture chamber and a vacuum port or an ambient pressure port to regulate pressure within the substrate capture chamber in relation to the ambient pressure surrounding the substrate capture chamber and a thread carrier driver disposed to axially move a thread carrier carrying a thread between a retracted condition disposing the thread carrier outside of the substrate capture chamber and an extended condition in which a thread carrier terminal end of the thread carrier passes axially through the substrate capture chamber into a thread capture chamber to engage a thread capture assembly which captures the thread to generate a thread loop upon return of the thread carrier toward the retracted condition.

Naturally, further objects of the invention are disclosed throughout other areas of the specification, drawings, photographs, and claims.

III. A BRIEF DESCRIPTION OF THE DRAWINGS

FIG. 7 is a first side elevation view of a particular embodiment of the suturing apparatus.

FIG. 8 is a second side elevation view of a particular embodiment of the suturing apparatus.

FIG. 16 is perspective view of a particular embodiment of the thread carrier.

Figure 22A:
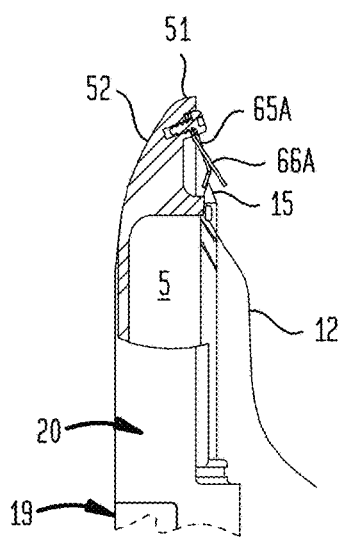
Figure 22B:
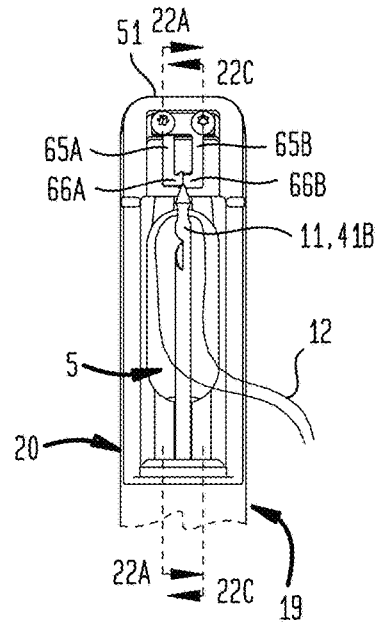

FIG. 22A is the cross section view 22A-22A shown in FIG. 22B depicting the unidirectional movement of the thread carrier in response to operation of the ratchet assembly to a thread carrier second position in which the thread carrier passes through the substrate capture chamber into the thread capture chamber and prohibited from being retracted back to the thread carrier first position within the handle of the suture apparatus.

FIG. 22B is a top plan view of the suturing probe having the top portion removed to depict the unidirectional movement of the thread carrier in response to operation of the ratchet assembly to a thread carrier second position in which the thread carrier passes through the substrate capture chamber into the thread capture chamber and prohibited from being retracted back to the thread carrier first position within the handle of the suture apparatus.

Figure 22C:
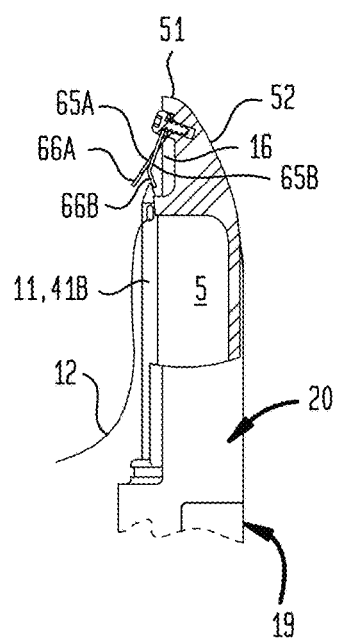

FIG. 22C is the cross section view 22C-22C shown in FIG. 22B depicting the unidirectional movement of the thread carrier in response to operation of the ratchet assembly to a thread carrier second position in which the thread carrier passes through the substrate capture chamber into the thread capture chamber and prohibited from being retracted back to the thread carrier first position within the handle of the suture apparatus.

Figure 23A:
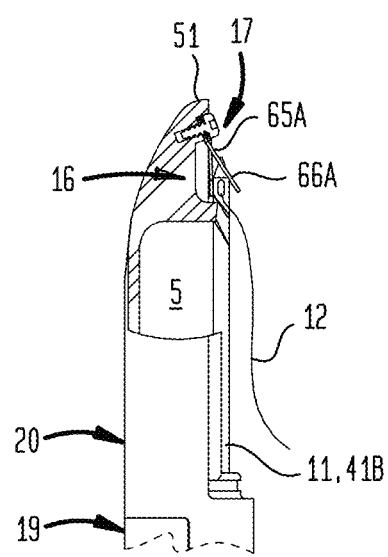
Figure 23B:
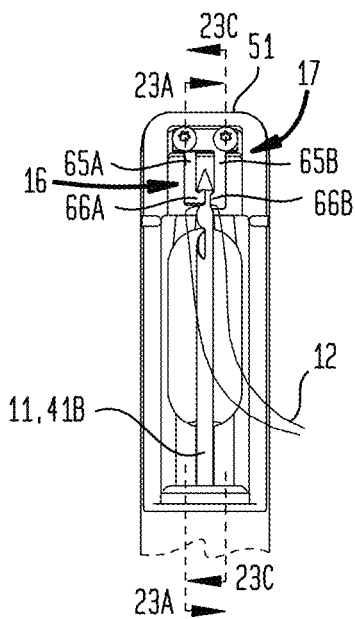

FIG. 23A is the cross section view 23A-23A shown in FIG. 23B depicting the unidirectional movement of the thread carrier in response to operation of the ratchet assembly toward a thread carrier third position in which the thread carrier passes through the substrate capture chamber into the thread capture chamber to engage the thread capture assembly.

FIG. 23B is a top plan view of the suturing probe having the top portion removed to depict the unidirectional movement of the thread carrier in response to operation of the ratchet assembly toward a thread carrier third position in which the thread carrier passes through the substrate capture chamber into the thread capture chamber to engage the thread capture assembly.

Figure 23C:
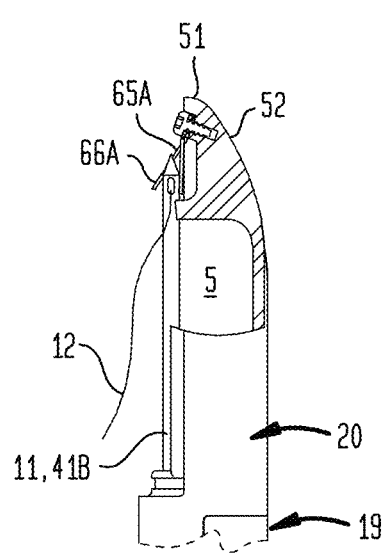

FIG. 23C is the cross section view 23C-23C shown in FIG. 23B depicting the unidirectional movement of the thread carrier in response to operation of the ratchet assembly toward a thread carrier third position in which the thread carrier passes through the substrate capture chamber into the thread capture chamber to engage the thread capture assembly.

Figure 24A:
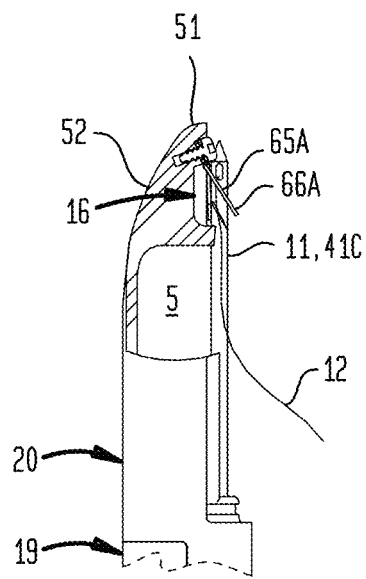
Figure 24B:
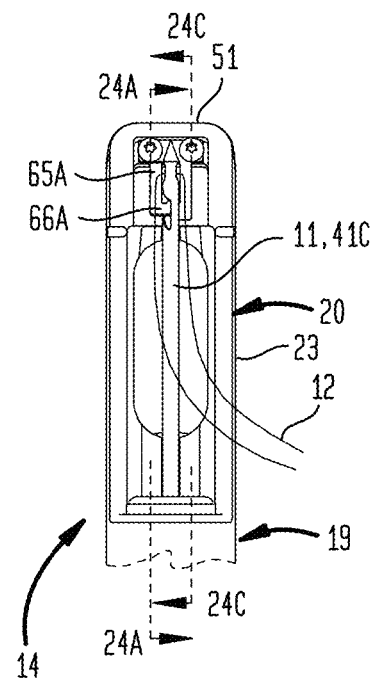

FIG. 24A is the cross section view 24A-24A shown in FIG. 24B depicting the unidirectional movement of the thread carrier in response to operation of the ratchet assembly to a thread carrier third position in which the thread carrier passes through the substrate capture chamber into the thread capture chamber to engage the thread capture assembly with a hook aligned in a notch passage.

FIG. 24B is top plan view of the suturing probe having the top portion removed to depict the unidirectional movement of the thread carrier in response to operation of the ratchet assembly to a thread carrier third position in which the thread carrier passes through the substrate capture chamber into the thread capture chamber to engage the thread capture assembly with a hook aligned in a notch passage.

Figure 24C:
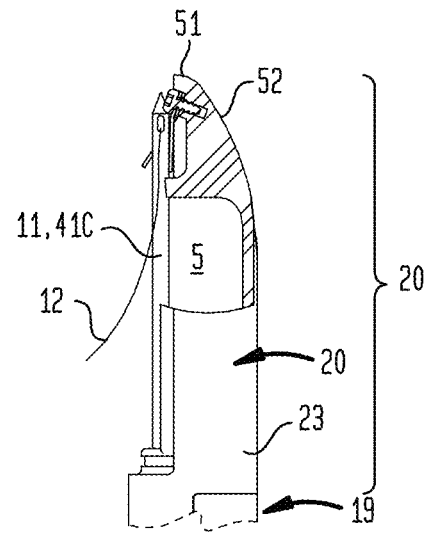

FIG. 24C is the cross section view 24C-24C shown in FIG. 24B depicting the unidirectional movement of the thread carrier in response to operation of the ratchet assembly to a thread carrier third position in which the thread carrier passes through the substrate capture chamber into the thread capture chamber to engage the thread capture assembly with a hook aligned in a notch passage.

Figure 25A:
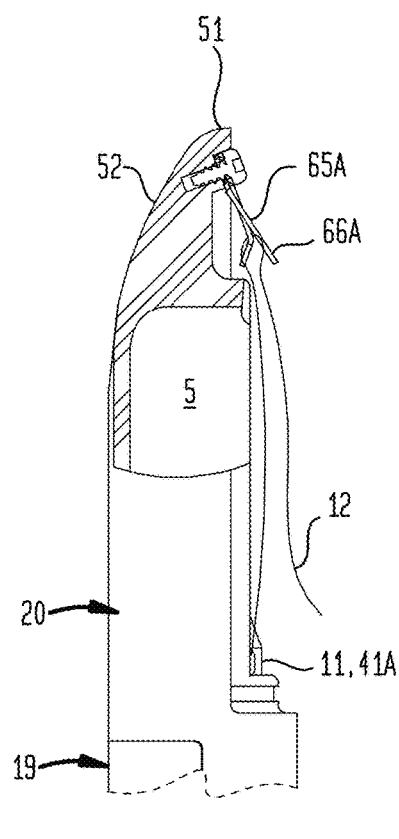
Figure 25B:
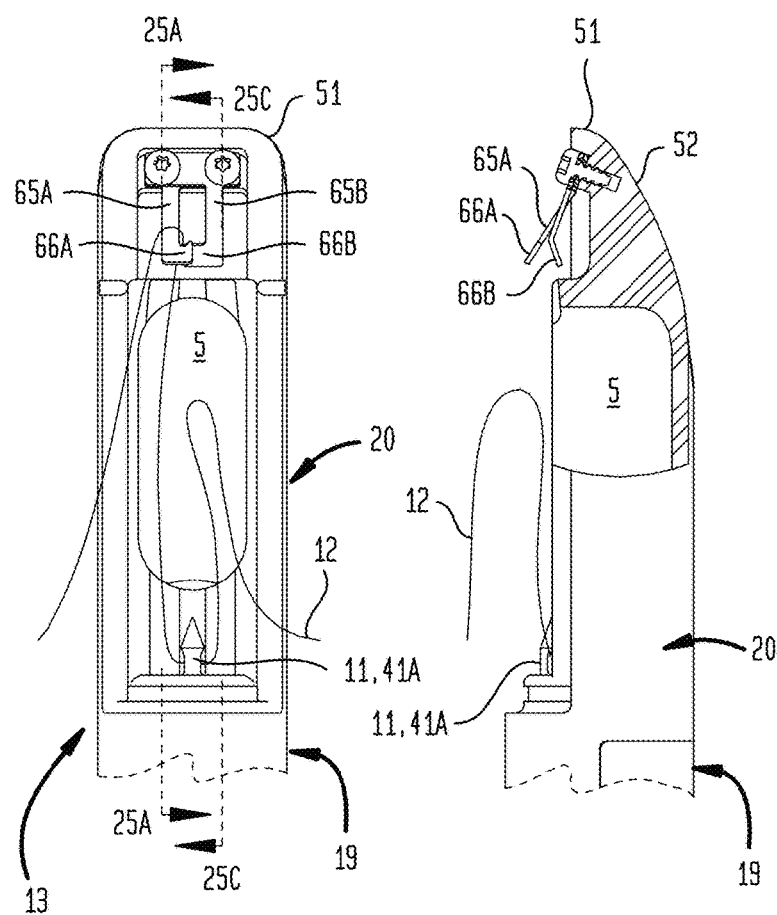

FIG. 25A is the cross section view 25A-25A shown in FIG. 25B depicting the retraction of the thread carrier in response to operation of the ratchet assembly to a thread carrier first position in which the thread carrier disengages the thread capture assembly passing through the substrate capture chamber into the handle forming a thread loop.

FIG. 25B is a top plan view of the suturing probe having the top portion removed to depict the retraction of the thread carrier in response to operation of the ratchet assembly to a thread carrier first position in which the thread carrier disengages the thread capture assembly passing through the substrate capture chamber into the handle forming a thread loop.

Figure 25C:
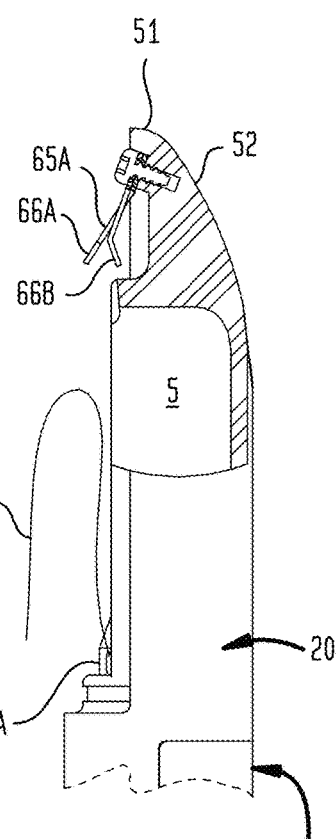

FIG. 25C is the cross section view 25C-25C shown in FIG. 25B depicting the retraction of the thread carrier in response to operation of the ratchet assembly to a thread carrier first position in which the thread carrier disengages the thread capture assembly passing through the substrate capture chamber into the handle forming a thread loop.

Figure 26:
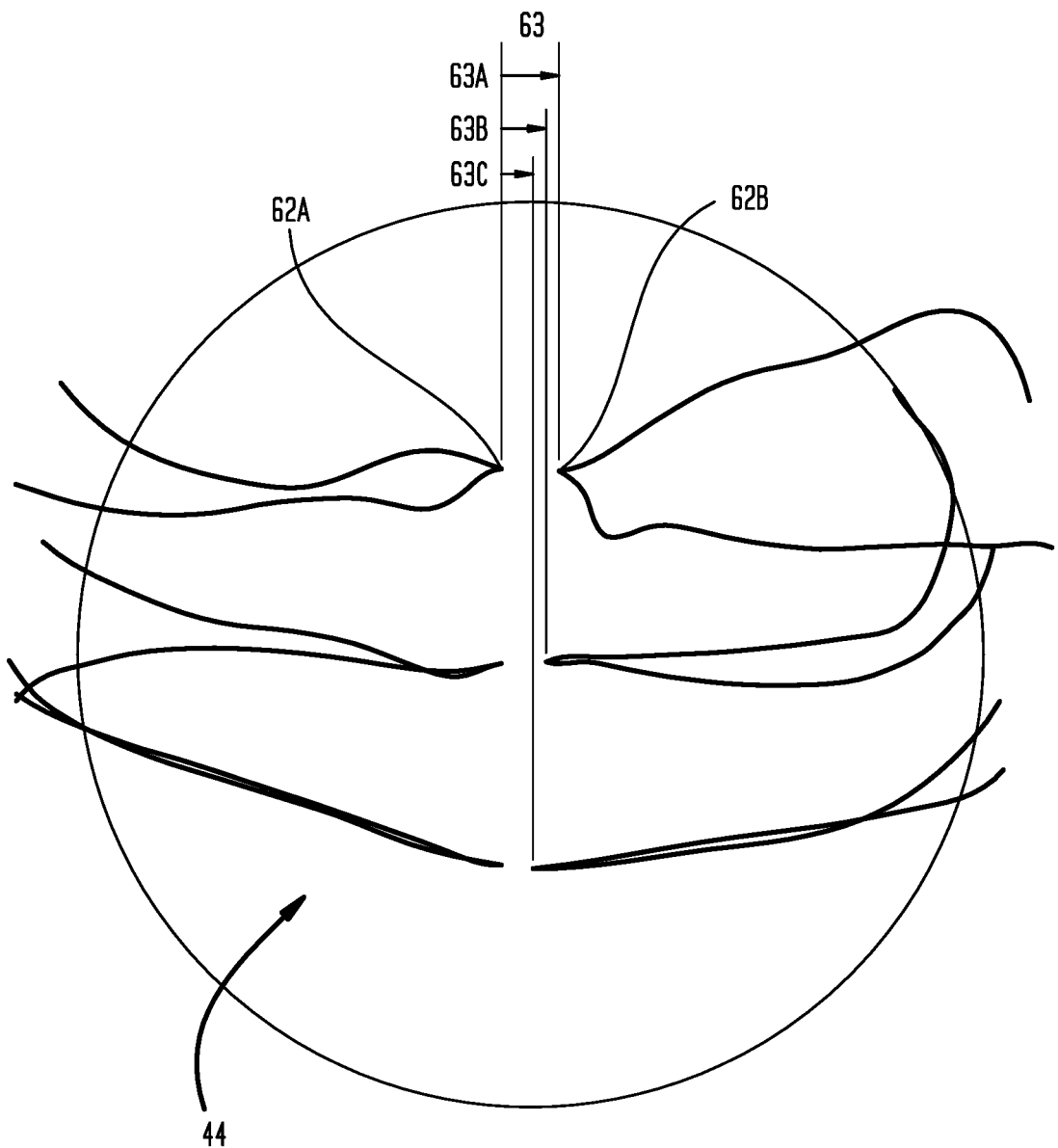

FIG. 26 is an illustration which compares the suture purchase of the inventive suturing apparatus of the particular embodiment shown in FIGS. 1 through 25 with conventional suturing apparatus.

IV. DETAILED DESCRIPTION OF THE PREFERRED EMBODIMENTS

Generally referring to FIGS. 1 through 26, embodiments of a suturing apparatus (1) including one or more of: a housing (2) which maintains in operable relation a valved conduit (3) operable to regulate fluid flow (4) between a substrate capture chamber (5) and a vacuum port (6) or an ambient pressure port (7) to regulate pressure (8) within the substrate capture chamber (5) in relation to the ambient pressure (9) surrounding the substrate capture chamber (5) and a thread carrier driver (10) disposed to axially move a thread carrier (11) carrying a thread (12) between a retracted condition (13) disposing the thread carrier (11) outside of the substrate capture chamber (5) and an extended condition (14) in which a thread carrier terminal end (15) of the thread carrier (11) passes axially through the substrate capture chamber (5) into a thread capture chamber (16) to engage a thread capture assembly (17) which captures the thread (12) to generate a thread loop upon return of the thread carrier (11) toward the retracted condition (13).

Now referring primarily to FIGS. 1 through 12, embodiments of the housing (2) can include a handle (18) and a tubular member (19) which outwardly axially extends from the handle (18) terminating in a suturing probe (20). The handle external surface (21) can, but need not necessarily, be configured to be grippingly engaged by the human hand. The tubular member external surface (22) and the suturing probe external surface (23) can, but need not necessarily, be configured to pass through small incisions or natural body openings to engage the deep surface of the skin, fascia, fat, or muscle of a patient. Accordingly, the handle (18), the tubular member (19), and the suturing probe (20) can be scaled depending upon the application.

Figure 1:
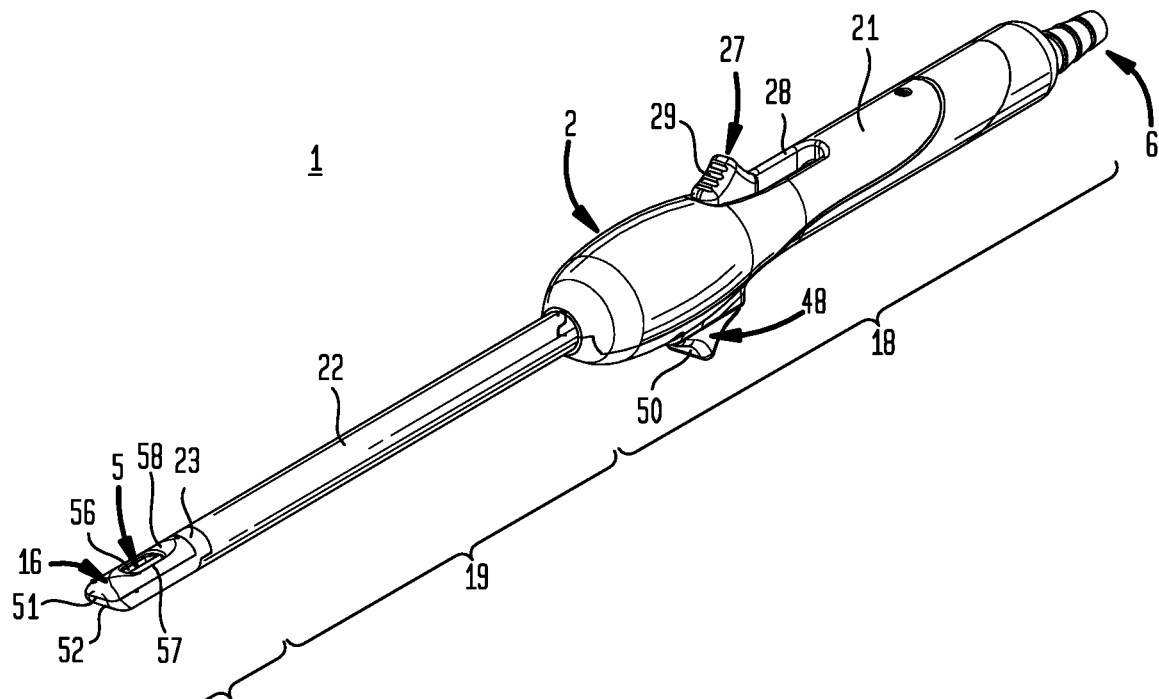
FIG. 1 is a first perspective view of a particular embodiment of a suturing apparatus.
Figure 2:
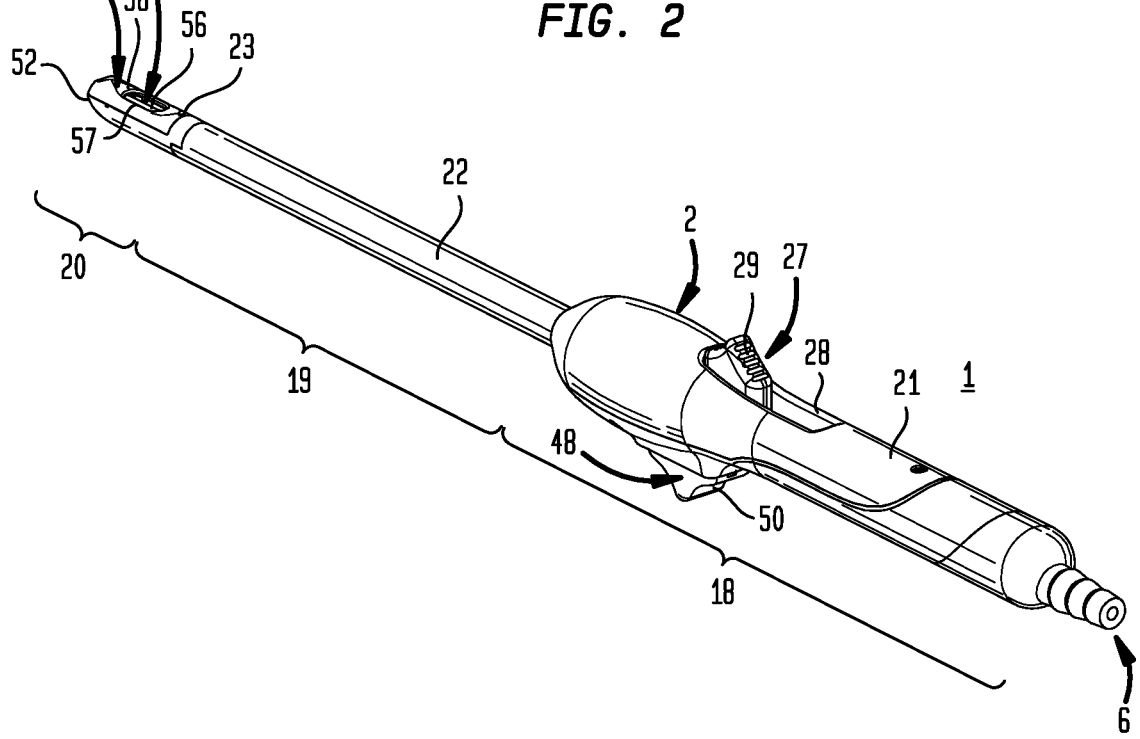
FIG. 2 is a second perspective view of a particular embodiment of the suturing apparatus.
Figure 3:
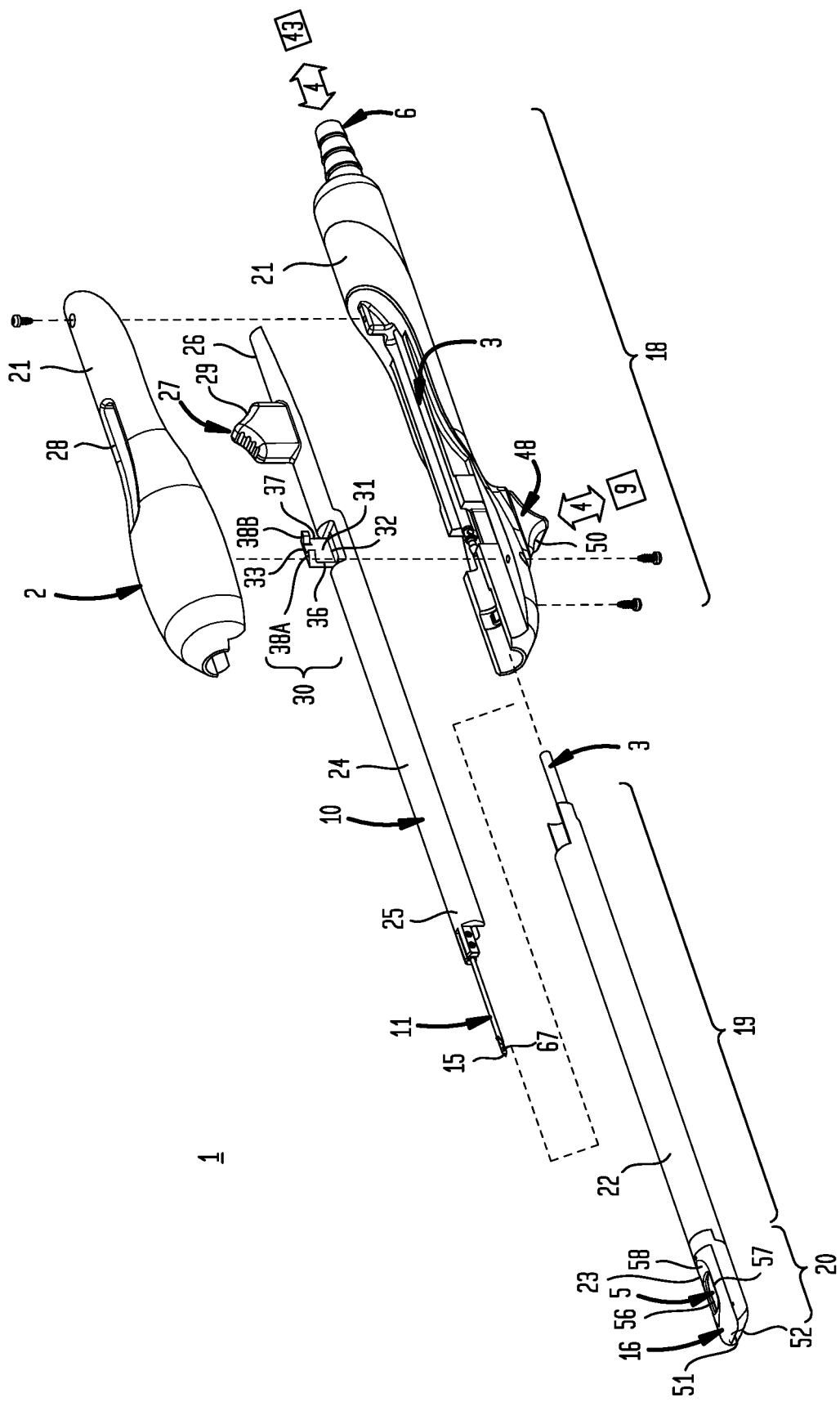
FIG. 3 is an exploded view of a particular embodiment of the handle of the suturing apparatus shown in FIGS. 1 and 2.

Now referring primarily to FIG. 3, the housing (2) can receive in axial sliding engagement a thread carrier driver (10). The thread carrier driver (10) comprises an elongate drive member (24) having a length disposed between a drive member first end (25) and a drive member second end (26). The elongate drive member (24) moves axially inside of the handle (18) in response to a drive member actuator (27). As to particular embodiments, a drive member actuator slot (28) can be disposed in the housing (2) and the drive member actuator (27) can be configured to extend through the drive member actuator slot (28) to present a pressable drive member actuator button (29) which upon forcible urging generates corresponding axial movement of the elongate drive member (24) inside of the handle (18).

Figure 6:
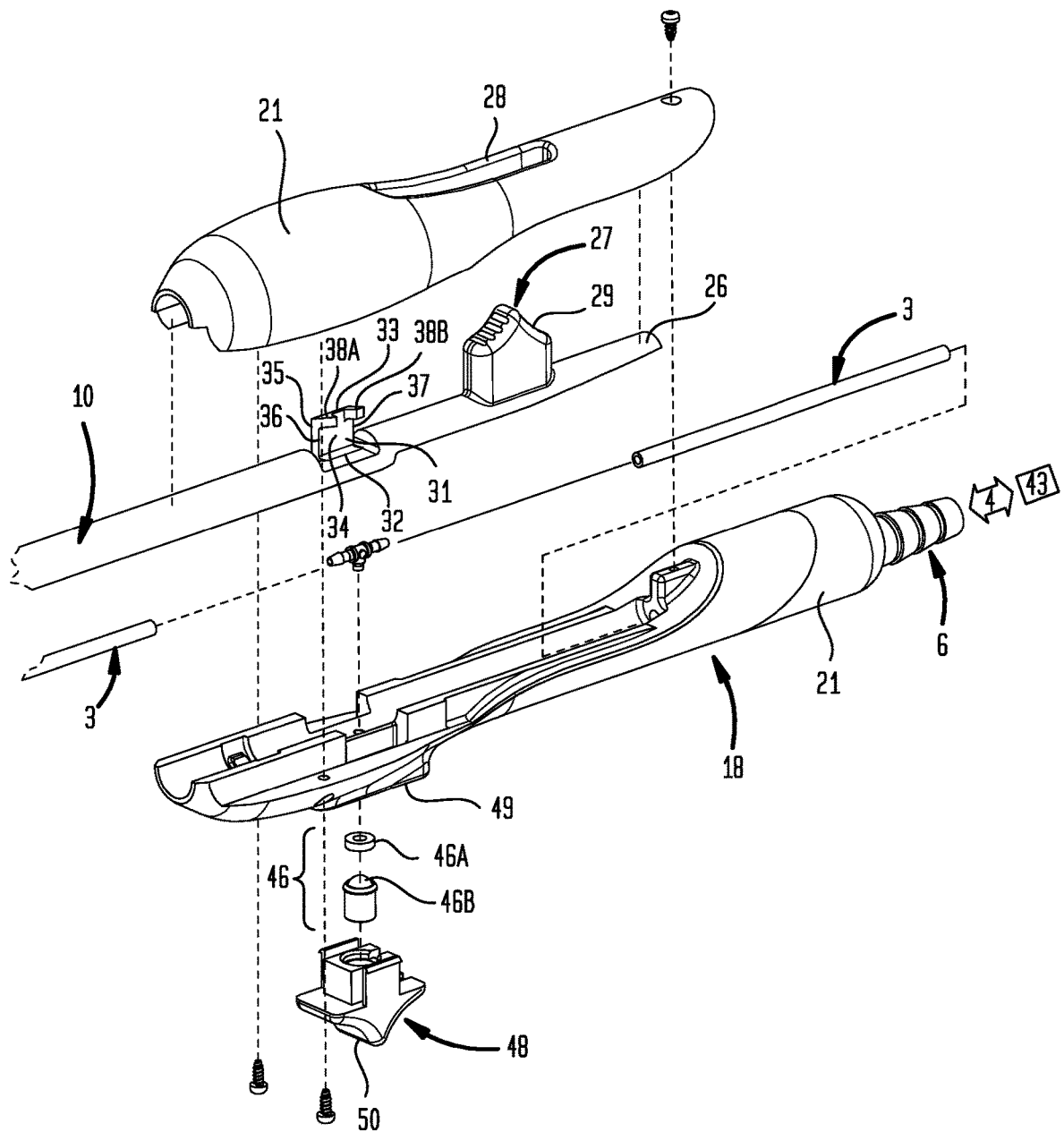
FIG. 6 is an exploded view of a particular embodiment of the valve actuator of the suturing apparatus shown in FIGS. 1 and 2.
Figure 9:
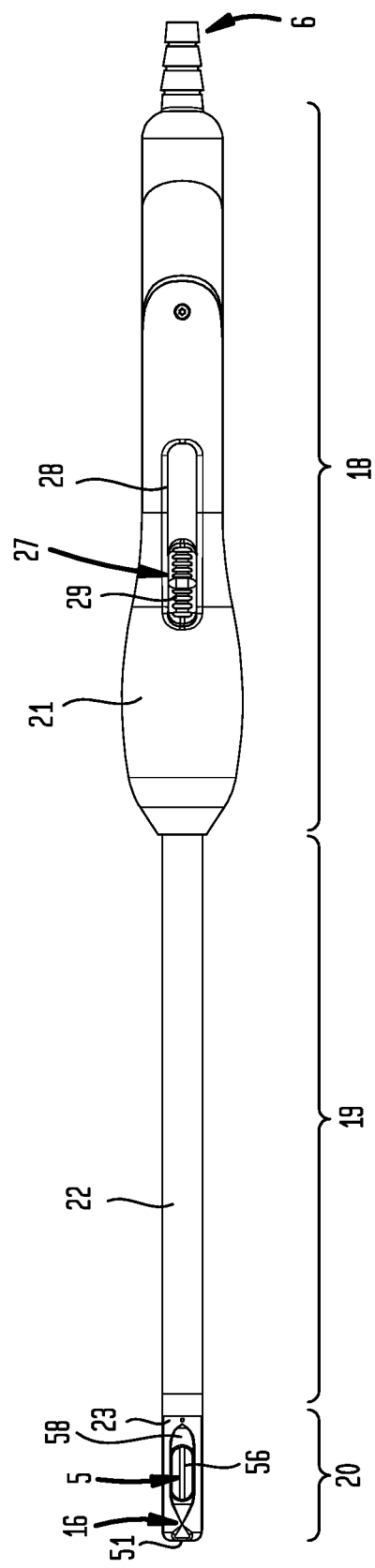
FIG. 9 is a top plan view of a particular embodiment of the suturing apparatus.
Figure 10:
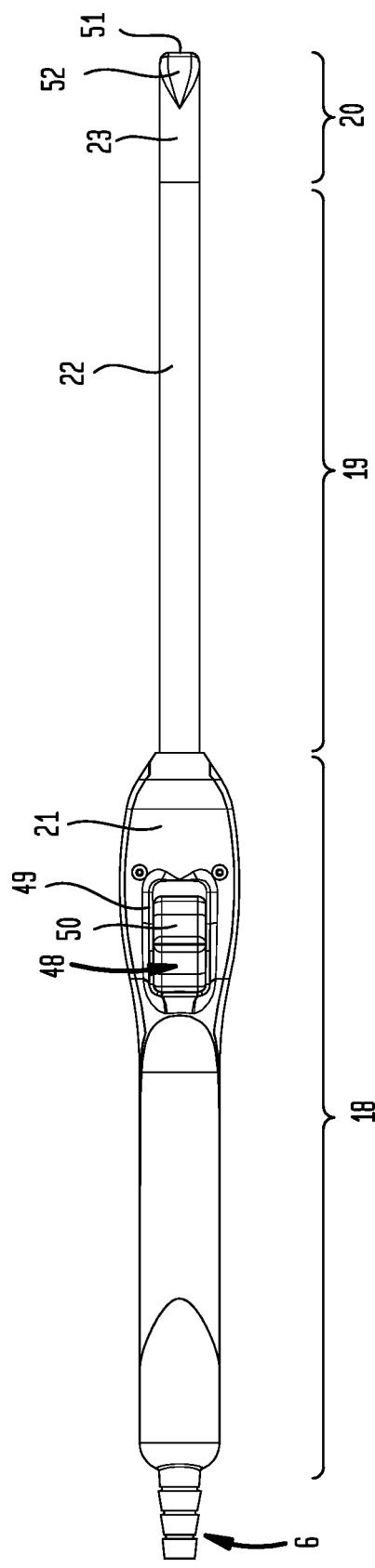
FIG. 10 is a bottom plan view of a particular embodiment of the suturing apparatus.
Figure 11:
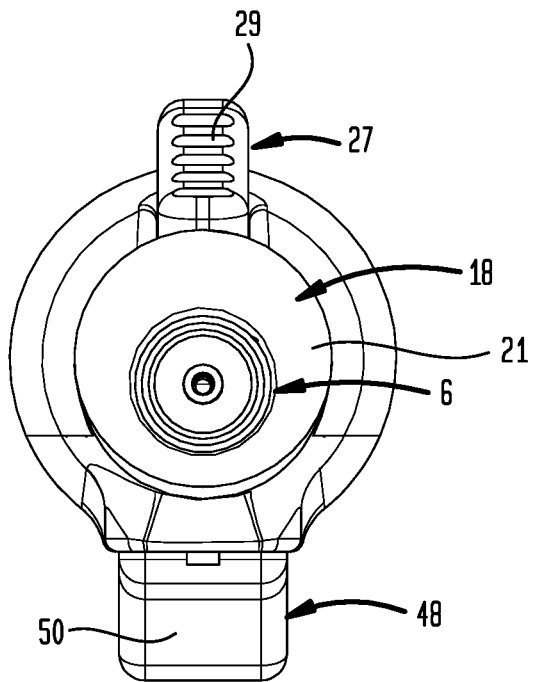
FIG. 11 is a first end view of a particular embodiment of the suturing apparatus.
Figure 12:
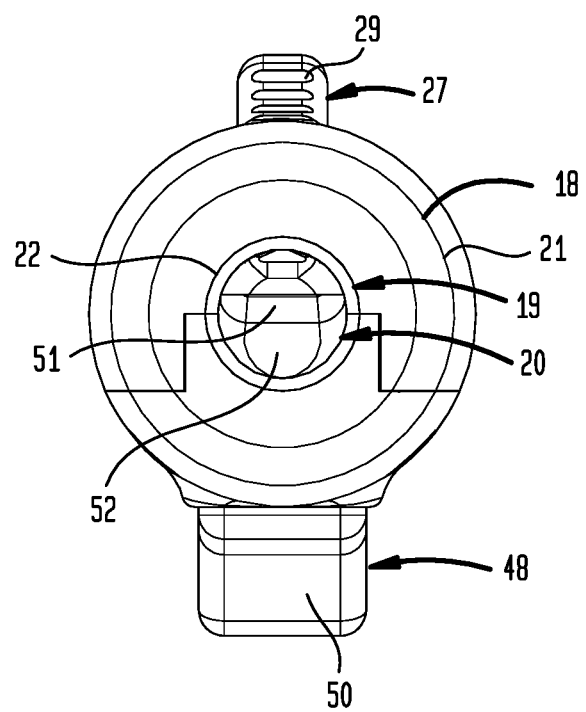
FIG. 12 is as second end view of a particular embodiment of the suturing apparatus.

Now referring primarily to FIGS. 3, 6, 13A, 13B and 13D, and 14B and 14D, particular embodiments of the thread carrier driver (10) can further include a ratchet assembly (30). The ratchet assembly (30) can comprise a resiliently flexible ratchet member (31) having a length disposed between a member first end (32) coupled to the elongate drive member (24) and extending outwardly to terminate in a member second end (33). The resiliently flexible ratchet member (31) can have a first face (34) opposite a second face (35) joined at the periphery by a leading edge (36) opposite a trailing edge (37). At least one angled tooth (38) can outwardly extend from the first face (34) proximate the member second end (33). As to particular embodiments, as shown in the examples of FIGS. 3 and 6, a pair of angled teeth (38A)(38B) can outwardly extend from the first face (34) proximate the member second end (33). A peg (39) having a fixed location on the housing internal surface (40) extends outwardly to engage the flexible member second end (33).

Figure 13A:
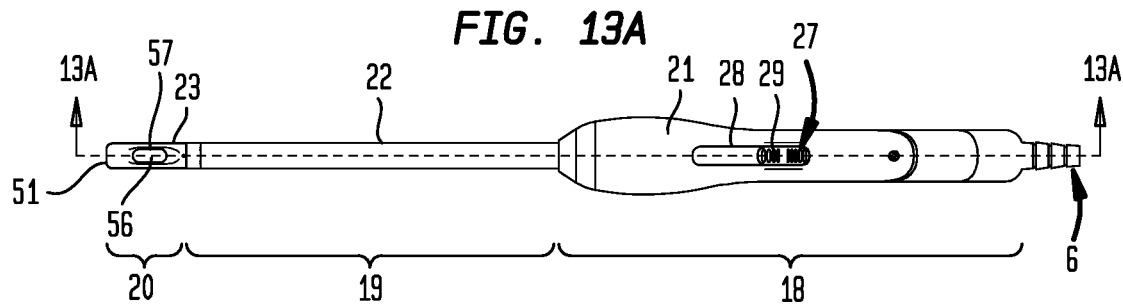
FIG. 13A is a top plan view of a particular embodiment of the suturing apparatus depicting the location of cross section 13A-13A.
Figure 13B:
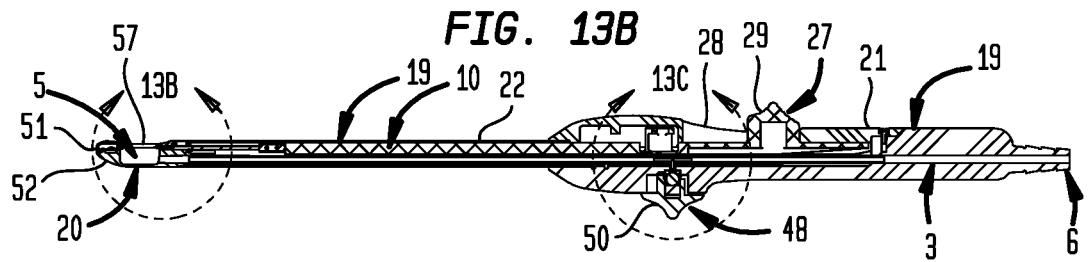
FIG. 13B is a cross section view 13A-13A as shown in FIG. 13.
Figure 13C:
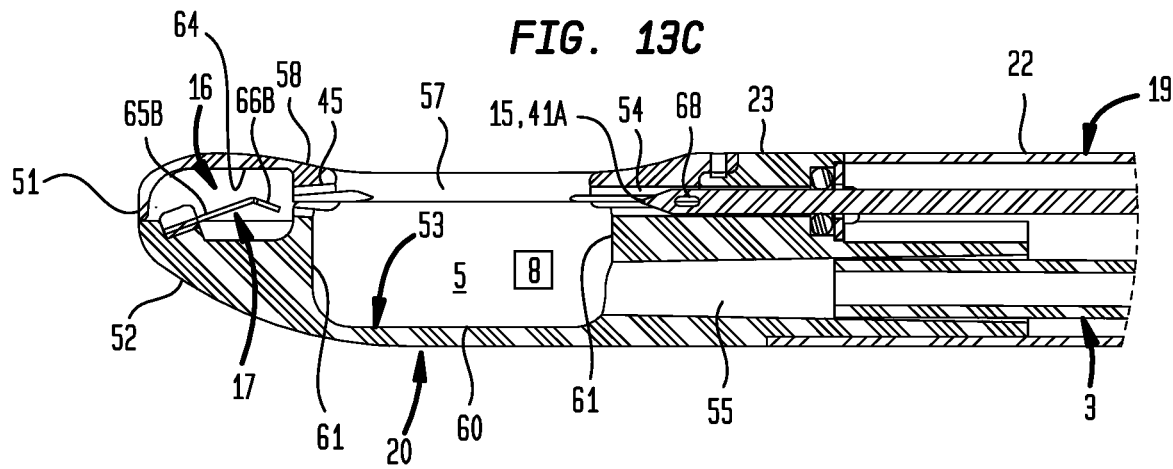
FIG. 13C is an enlarged view of portion 13B shown in FIG. 13A which depicts the thread carrier in a first thread carrier position retracted within the handle outside of the substrate capture chamber.
Figure 13D:
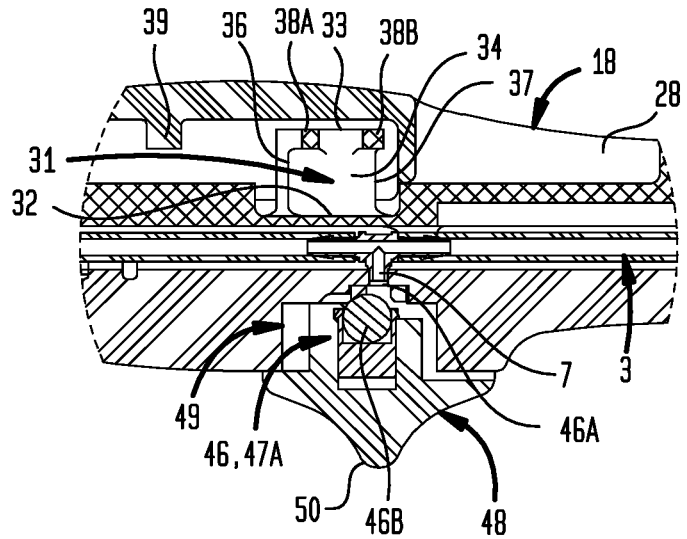
FIG. 13D is an enlarged view of portion 13C shown in FIG. 13A having the ambient pressure port in the open condition.
Figure 14A:
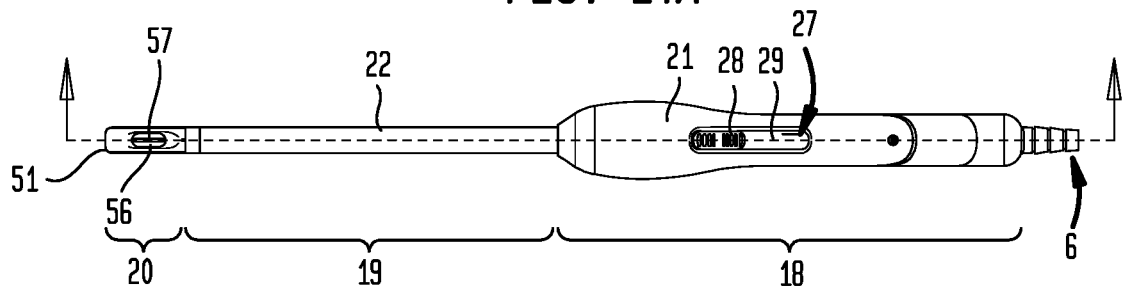
FIG. 14A is a top plan view of a particular embodiment of the suturing apparatus depicting the location of cross section 14A-14A.
Figure 14B:
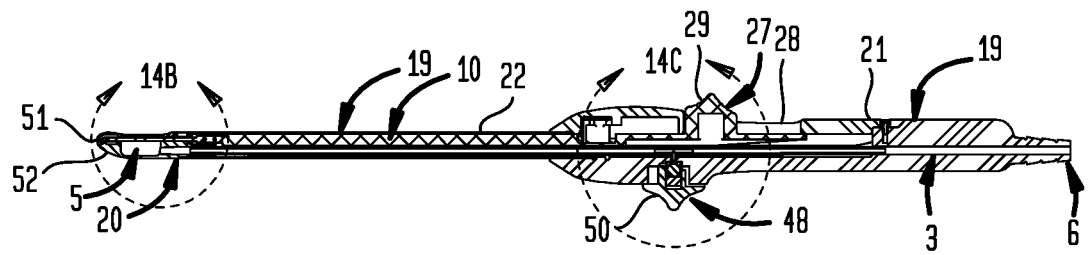
FIG. 14B is a cross section view 14A-14A as shown in FIG. 14A.
Figure 14C:
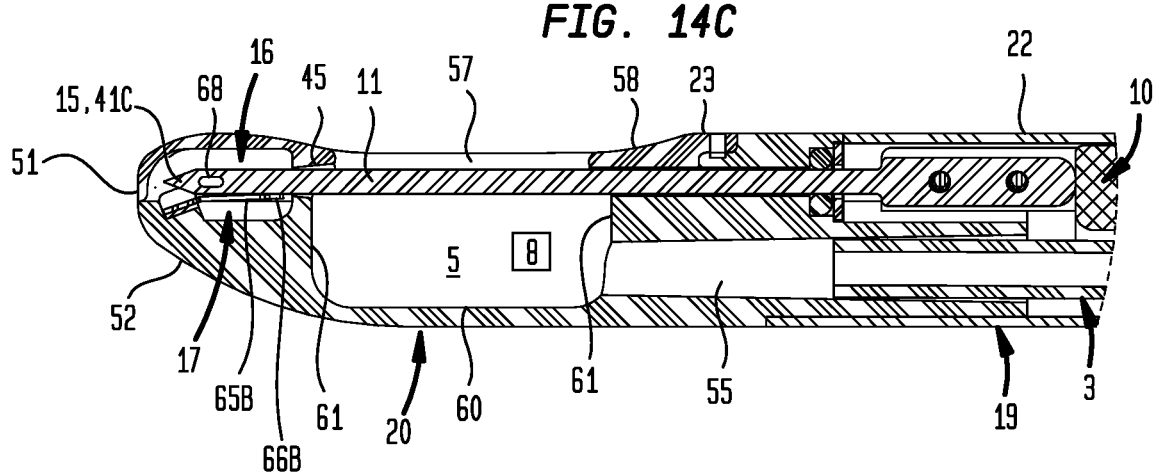
FIG. 14C is an enlarged view of portion 14B shown in FIG. 14A which depicts the thread carrier in a third thread carrier position extended to pass through the substrate capture chamber into the thread capture chamber to engage a thread capture assembly.
Figure 14D:
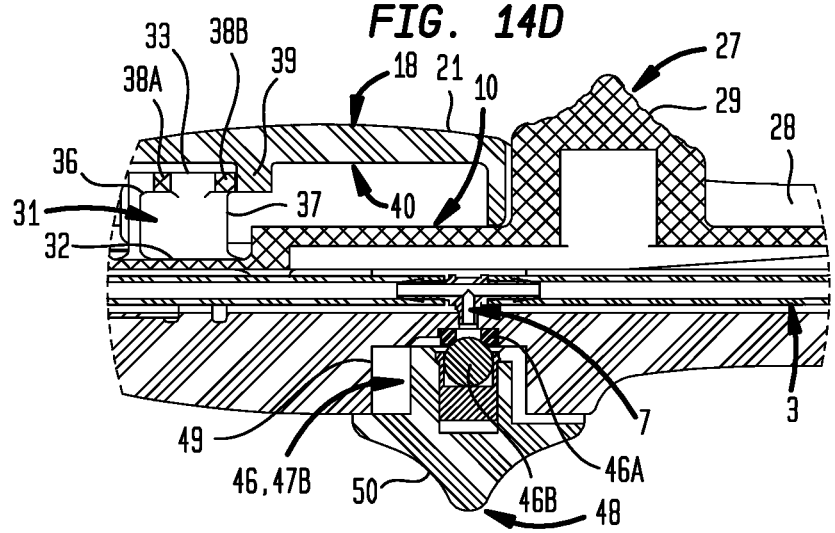
FIG. 14D is an enlarged view of portion 14C shown in FIG. 14A having the ambient pressure port in the closed condition.
Figure 15A:
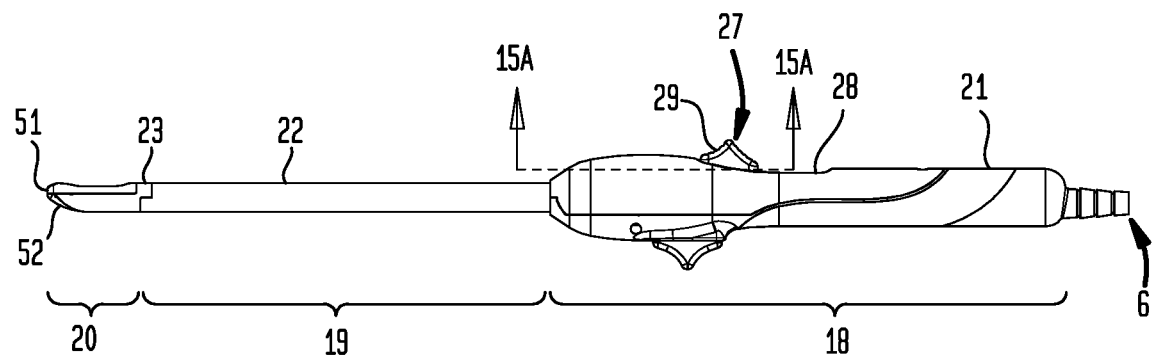
FIG. 15A is a first side elevation view of a particular embodiment of the suturing apparatus depicting the location of cross section 15A-15A.
Figure 15B:
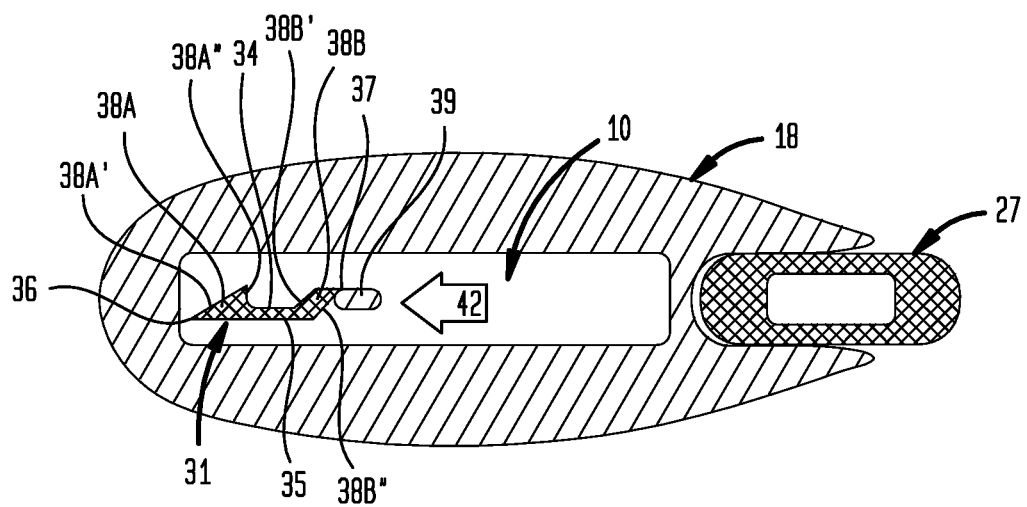
FIG. 15B is a cross section view 15A-15A as shown in FIG. 15A.

Now referring primarily to FIGS. 13D and 14D, the thread carrier driver (10) can be slidably axially moved in the housing (2) to concurrently axially move the thread carrier (11) and the resiliently flexible ratchet member (31). The peg (39) can have a location proximate the leading edge (36) of the resiliently flexible ratchet member (31) (as shown in the example of FIG. 13D) to dispose the thread carrier terminal end (15) at a thread carrier first position (41A) outside of the substrate capture chamber (5). The resiliently flexible ratchet member (31) flexes in a first direction (42A) to allow at least one angled tooth (38) or the first of a pair of angled teeth (38A) (or the first of a plurality of angled teeth) to unidirectionally slidably engage the peg (39) over the first tooth angled face (38A') to dispose the peg (39) adjacent the corresponding first tooth base (38A") or between the pair of angled teeth (38A)(38B) adjacent the first tooth base (38A") and to concurrently dispose the thread carrier terminal end (15) at a thread carrier second position (41B) inside of the substrate capture chamber (5). Once the peg (39) traverses the first tooth angled face (38A') of at least one angled tooth (38) toward the trailing edge (37) of the resiliently flexible ratchet member (31), the resiliently flexible ratchet member (31) returns toward the unflexed position to dispose the peg (39) adjacent the first tooth base (38A'), which prohibits the peg (39) from traveling toward the leading edge (36) of the resiliently flexible ratchet member (31).

Now referring primarily to FIG. 14D, the peg (39) can be disposed between a pair of angled teeth (38A)(38B) adjacent the first tooth base (38A') of the first of the pair of angled teeth (38A). The resiliently flexible ratchet member (31) again flexes in the first direction (42A) to allow a second of the pair of teeth (38B) to unidirectionally slidably engage the peg (39) with the second tooth angled face (38B') to dispose the peg (39) adjacent the second tooth base (38B") of the second of the pair of angled teeth (38B) and to concurrently dispose the thread carrier terminal end (15) at a third thread carrier position (41C) in the thread capture chamber (16). The second tooth base (38B") (or the tooth proximate the trailing edge (37) of the resiliently flexible ratchet member (31)) can be angled to flex the resiliently flexible member (31) in a second direction (42B) to allow the member second face (33) to unidirectionally slidably engage the peg (39) to position the peg (29) a distance away from the leading edge (36) of the resiliently flexible ratchet member (31) and concurrently dispose the thread carrier terminal end (15) at the thread carrier first position (41A) at a location outside of the substrate capture chamber (5).

Now referring primarily to FIGS. 3, 6, 13B, 13C, and 13D, the housing (2) can be configured to provide a vacuum port (6) opening on the handle external surface (21) (as shown in the example of FIGS. 3 and 6). The vacuum port (6) can be coupled to a vacuum source (43) (as shown in the example of FIGS. 3 and 6). The vacuum source (43) can comprise any of a variety of conventional vacuum or suction pumps. The valved conduit (3) can be connected between the vacuum port (6) and the substrate capture chamber (5) (as shown in the examples of FIGS. 3, 13B and 13C). The vacuum source (43) can be operated to generate a reduced chamber pressure (8) in the substrate capture chamber (5). As to particular embodiments, the reduced chamber pressure (8) can be sufficient to draw a fold of a substrate (44) or a pair of layers of the substrate (44), or a plurality of layers of the substrate (44) into the substrate capture chamber (5). The housing (2) can be further configured to provide an ambient pressure port (7) opening on the handle external surface (21) to ambient pressure (9). The valved conduit (3) can be operated to regulate fluid flow (4) between the vacuum port (6) and the substrate capture chamber (5) or the ambient pressure port (7) to regulate chamber pressure (8) within the substrate capture chamber (5) in relation to the ambient pressure (9) surrounding said substrate capture chamber (5). The valved conduit (3) can include a valve (46) operable between an ambient pressure port closed condition (47B) in which fluid flow (4) occurs primarily between the substrate capture chamber (5) and the vacuum source (43) to generate reduced chamber pressure (8) in the substrate capture chamber (5) and an ambient pressure port open condition (46A) in which fluid flow occurs primarily between the ambient pressure port (7) and the vacuum source (43) generating ambient pressure (9) in the substrate capture chamber (5). As reduced chamber pressure (8) in the substrate capture chamber (5) approaches ambient pressure (9) the substrate (44) captured inside of the substrate capture chamber (5) can be released to a location outside of the substrate capture chamber (5).

Now referring primarily to FIGS. 6 and 13D and 14D, as to particular embodiments, the valve (46) can, but need not necessarily, include a valve seat (46A) surrounding the ambient pressure port (7) and a valve ball (46B) which can be positioned on the valve seat (46A) to generate the ambient pressure port closed condition (47B) (as shown in the example of 14D). The valve ball (46B) can be moved in relation to the valve seat (46A) to generate the ambient port open condition (47A) (as shown in the example of FIG. 13D). As to particular embodiments, the valved conduit (3) can further include a valve actuator (48) coupled to the valve (46). The valve actuator (48) can be moved to correspondingly position the valve ball (46B) between the ambient pressure port open position (47A) and the ambient pressure port closed condition (47B). As to particular embodiments, a valve actuator slot (49) can be disposed in the housing (2) and the valve actuator (48) can be configured to extend through the valve actuator slot (49) to present a pressable valve actuator button (50) of the valve member actuator (46) which upon forcible urging generates corresponding movement of the valve ball (46B) in relation to the valve seat (46A) to correspondingly provide the ambient pressure port open condition (47A) and the ambient pressure port closed condition (47B).

Now referring primarily to FIGS. 13A, 13B, 13C, 17A and 17B, embodiments of the suturing apparatus (1) further include a suturing probe (20) outward axially extending from the tubular member (19) to terminate in a probe tip (51). The suturing probe external surface (23) can, but need not necessarily, be configured as an extension of the external dimensions of the tubular member (29) allowing the probe tip (51) to pass through small incisions or natural body openings to engage the deep surface of the skin, fascia, fat, or muscle of a patient. As to particular embodiments, the suturing probe (20) can have a generally cylindrical suturing probe external surface (23) terminating in a hebetated probe tip (51). As to particular embodiments, the suturing probe external surface (23) can include a tapered, beveled, or sloped surface approaching the probe tip (51) to reduce dimensions at the probe tip (51). As to the particular embodiment shown in the example of FIG. 17B, the suturing probe external surface (23) can take the general form of a truncated cylinder in which a plane inclined in relation to the cylindrical axis of the suturing probe (20) generally defines an inclined probe face (52) terminating at the probe tip (51). There can be an advantage in an inclined probe face (52) as it allows the suturing probe (20) additional ingress in tissues with a lesser amount of tissue dissection or trauma.

Again, referring to FIGS. 13A, 13B, 13C, 17A and 17B, embodiments of the suturing probe (20) include a suturing probe internal surface (53) which can, but need not necessarily be, partitioned into an enclosed thread capture chamber (16) containing a thread capture assembly (17) adjacent a substrate capture chamber (5). The substrate capture chamber (5) can be connected to two longitudinal channels (54)(55). The thread carrier (11) reciprocally travels in the first longitudinal channel (54) in response to movement of the thread carrier driver (10). The second longitudinal channel (55) couples the substrate capture chamber (5) to the valved conduit (3) through which fluid flow (4) passes to regulate the chamber pressure (8) within the substrate capture chamber (5). The substrate capture chamber (5) has a chamber opening (56) defined by a chamber port (57) which communicates between the suturing probe internal surface (53) and the suturing probe external surface (23). As to particular embodiments, a recessed peripheral margin (58) can be disposed about the chamber port (57) of the suturing probe external surface (23). The recessed peripheral margin (58) can be configured to lessen the curvature of the suturing probe external surface (23) or to generate a substantially flat peripheral margin (58) about the chamber port (57) (as shown in the example of FIGS. 13B and 13C). The chamber port (57) can be engaged with a substrate (44), and a reduced chamber pressure (8) generated in the substrate capture chamber (5) can dispose or draw folds or layers of the substrate (44) into the substrate capture chamber (5). There can be an advantage in a recessed peripheral margin (58) about the chamber port (57) to increase the area of the suturing probe external surface (23) contacting the substrate (44) under reduced chamber pressure (8) in the substrate capture chamber (5) to decrease movement of the suturing probe (20) in relation to the captured substrate (44).

Figure 20A:
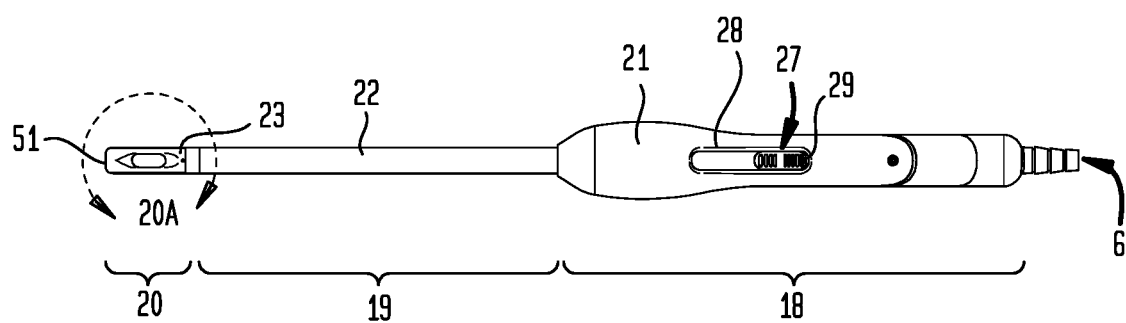
FIG. 20A is a top plan view showing the position of the thread carrier retracted into the handle of the suturing apparatus.
Figure 20B:
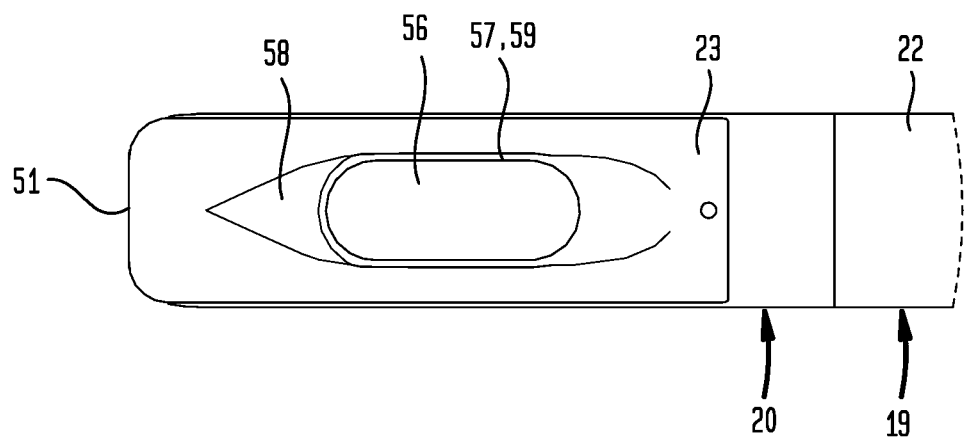
FIG. 20B is an enlarged view of the portion 20A shown in FIG. 20A showing the position of the thread carrier retracted into the handle of the suturing apparatus.

Now referring primarily to FIG. 20B, the chamber port (57) can, but need not necessarily, be disposed in a stadium configuration (59), being a rectangle with semicircles at a pair of opposite sides. Now referring primarily to FIGS. 13C and 17B, the substrate capture chamber (5) can, but need not necessarily, have a chamber bottom (60) in a stadium configuration disposed opposite the chamber port (57) in stadium configuration connected by a substantially vertical chamber sidewall (61). As to particular embodiments, the vertical chamber side wall (61) can define a periphery of greater circumference than the periphery of the chamber port (57) (also referred to as the "stadium configuration").

Now referring primarily to FIG. 26, there can be an advantage in a substrate capture chamber (5) of stadium configuration (59) in that an increased amount of substrate (44) can be penetrated by the thread carrier (11) to dispose a thread entry point (62A) and a thread withdraw point (62B) a greater distance apart (also referred to as the "suture purchase (63)") as compared to conventional slotted or cylindrical suction chambers. As shown in FIG. 26, the thread purchase (63) generated by use of the inventive substrate capture chamber (5) having a stadium configuration (59) (shown as suture purchase (63A)) is substantially greater than that obtained using a suction chamber of cylindrical configuration (suture purchase (63B)) or obtained using a conventional suction chamber of slotted configuration (thread purchase (63C)). It may be that the conventional cylindrical configuration draws the substrate into a conical configuration within the conventional cylindrical suction chamber and the conventional needle only penetrates the substrate proximate the apex of the cone. It may be that the conventional slotted suction chamber does not have sufficient volume to dispose the substrate a sufficient distance into the conventional slotted chamber and the conventional needle only penetrates the substrate layers in adjacent relation close to the fold or edges.

Now referring primarily to FIGS. 13C, 14C, 17B, and 18B, embodiments of the suturing probe internal surface (53) can define a thread capture chamber internal surface (64) defining the thread capture chamber (16). A thread carrier channel (45) communicating between the thread capture chamber (16) and the substrate capture chamber (5) allows ingress and egress of the thread carrier terminal end (15) into the thread capture chamber (16) (as shown by the example of FIGS. 13B, 14C, 17B and 18B).

Figure 4:
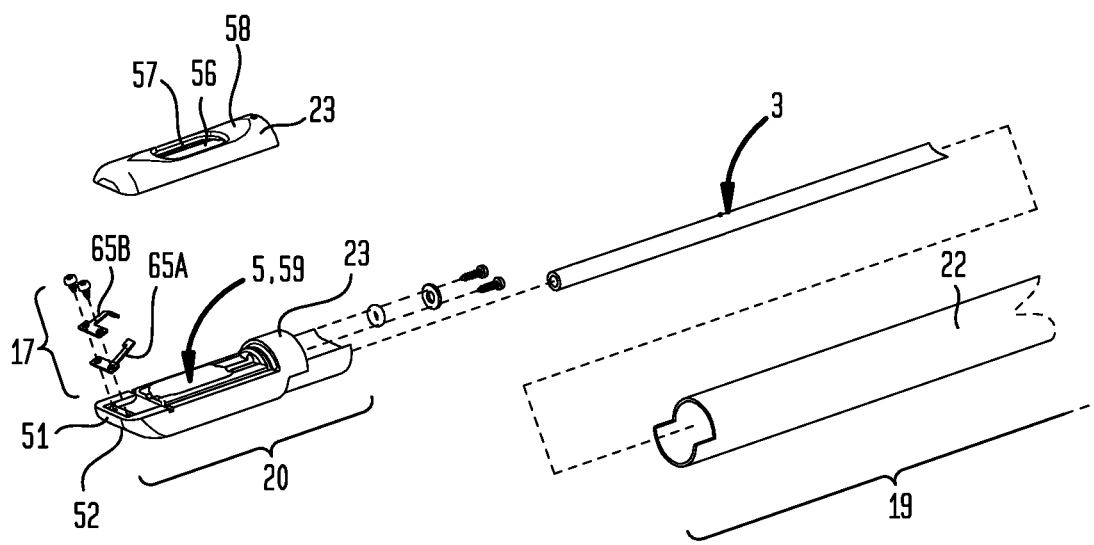
FIG. 4 is and exploded view of a particular embodiment of the suturing probe of the suturing apparatus shown in FIGS. 1 and 2.
Figure 17A:
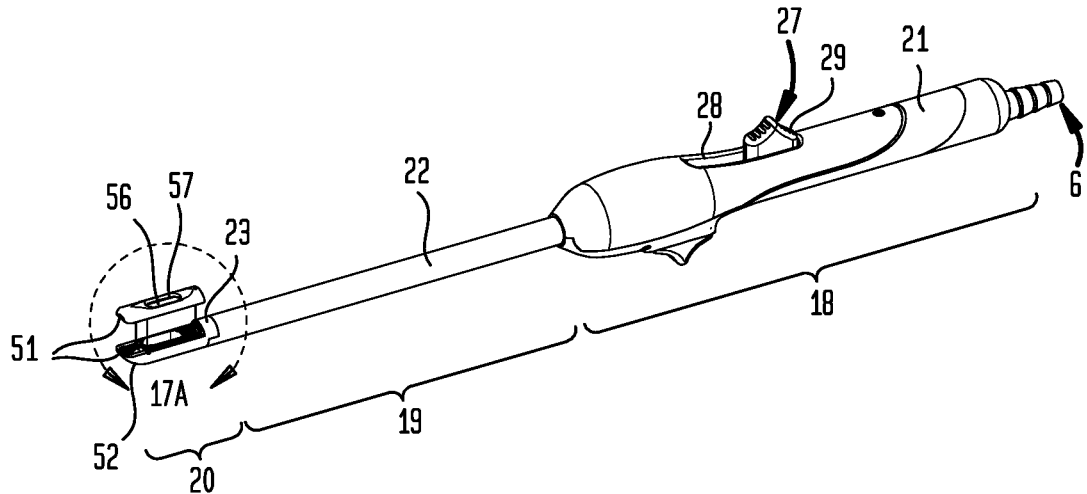
FIG. 17A is a first perspective view a particular embodiment of the suturing apparatus with an exploded view of the suturing probe showing the position of the thread carrier retracted in the handle of the suturing apparatus.
Figure 17B:
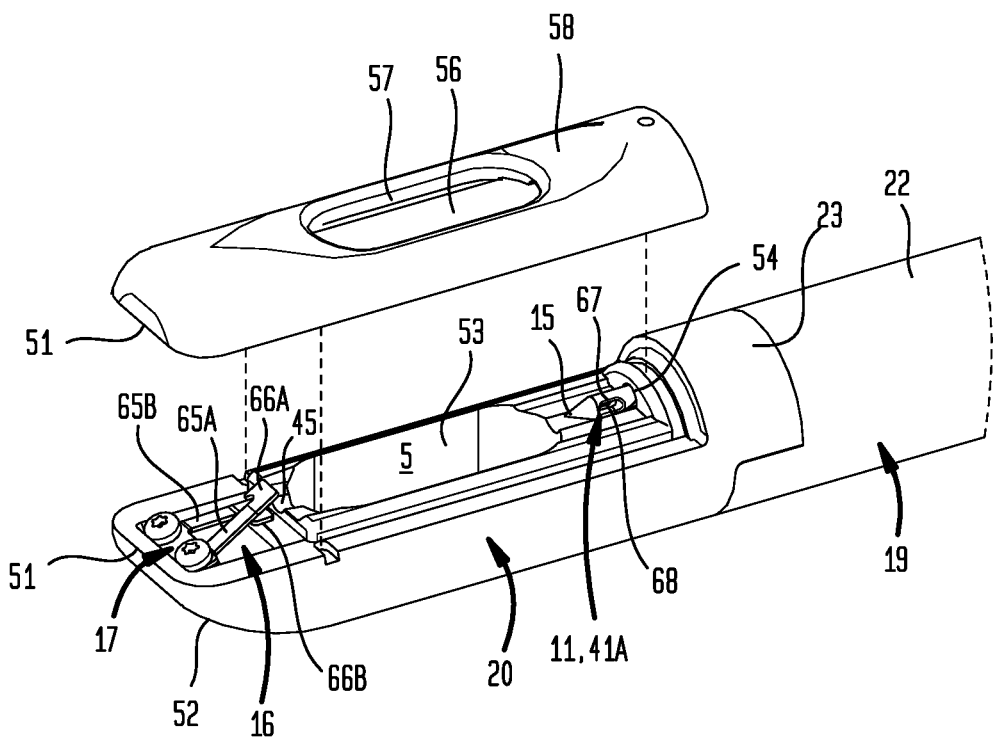
FIG. 17B is an enlarged view of the portion 17A shown in FIG. 17A showing the position of the thread carrier retracted in the handle of the suturing apparatus.
Figure 18A:
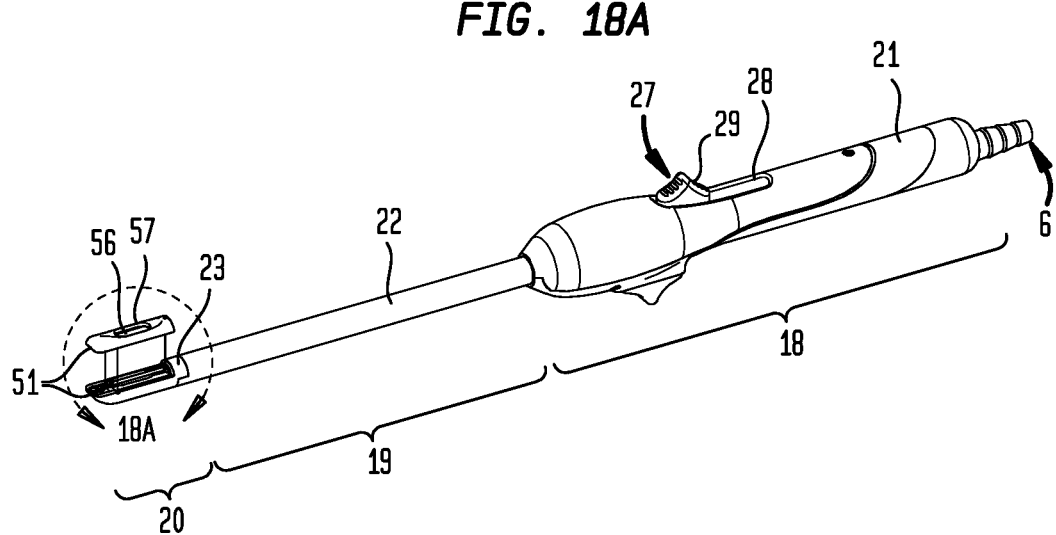
FIG. 18A is a first perspective view a particular embodiment of the suturing apparatus with an exploded view of the suturing probe showing the position of the thread carrier extended into the thread capture chamber and engaged with the thread capture assembly.
Figure 18B:
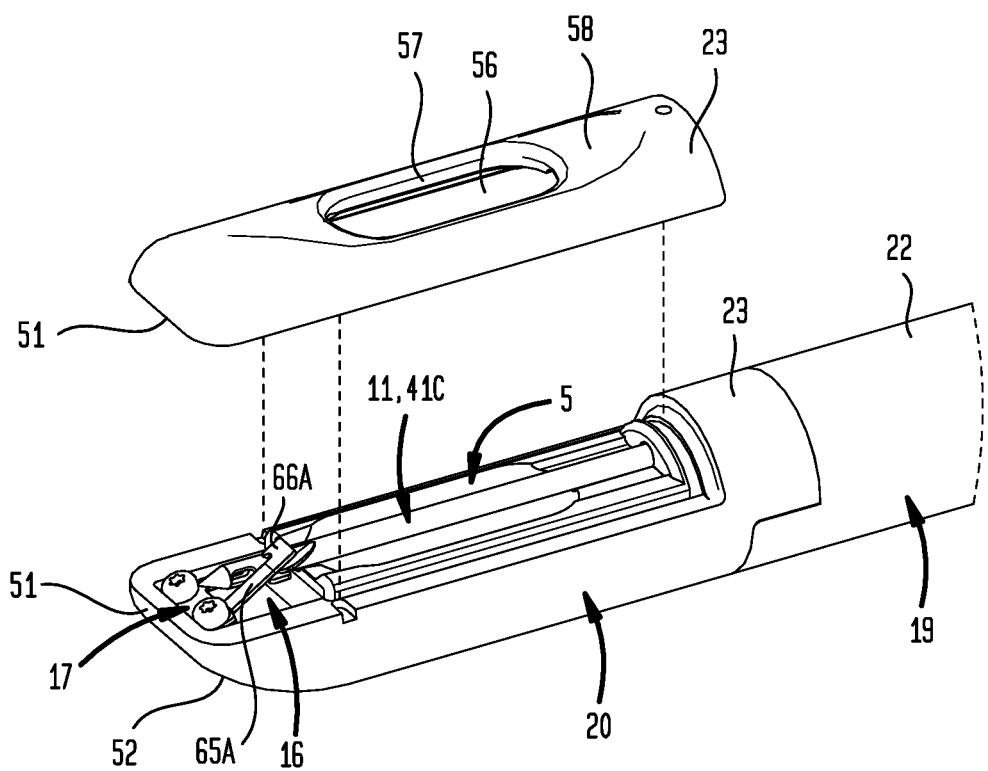
FIG. 18B is an enlarged view of the portion 18A shown in FIG. 18A showing the position of the thread carrier extended into the thread capture chamber and engaged with the thread capture assembly.
Figure 19A:
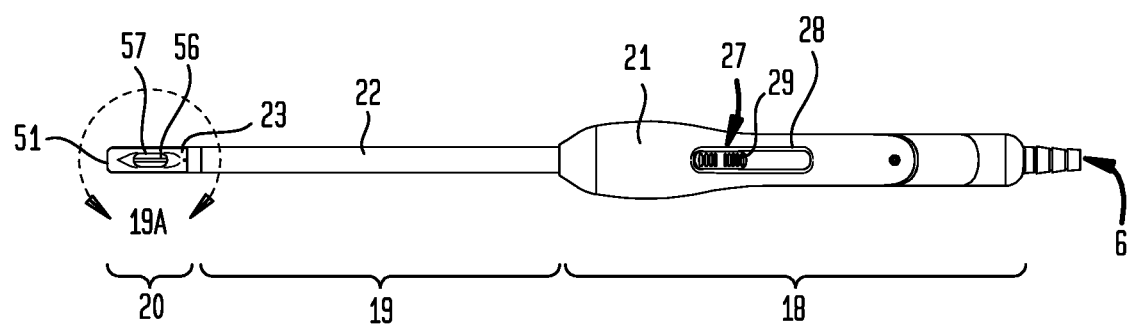
FIG. 19A is a top plan view showing the position of the thread carrier extended into the thread capture chamber and engaged with the thread capture assembly.
Figure 19B:
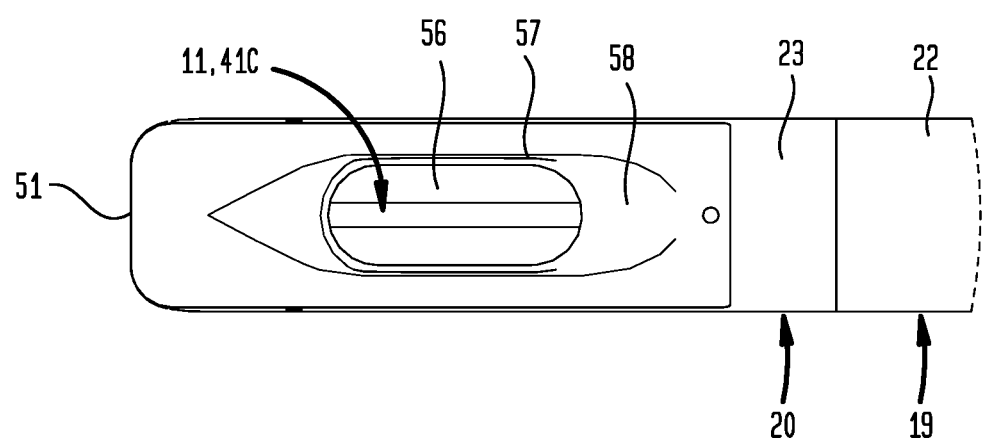
FIG. 19B is an enlarged view of the portion 19A shown in FIG. 19A showing the position of the thread carrier extended into the thread capture chamber and engaged with the thread capture assembly.

Now referring primarily to FIGS. 4 and 17B, a thread capture assembly (17) can be disposed in the thread capture chamber (16). The thread capture assembly (17) can include at least one resiliently flexible hook member (65A) correspondingly terminating in at least one hook (66A). The resiliently flexible hook member (65A) can be coupled to the thread capture chamber internal surface (64) to dispose the hook (66A) at a location to engage the thread carrier (11) and flexing the at least one resiliently flexible hook member (65A). As to particular embodiments, the thread capture assembly (17) can include a pair of resiliently flexible hook members (65A)(65B) each correspondingly terminating in one of a pair of hooks (66A)(66B). The pair of resiliently flexible hook members (65A)(65B) can each be coupled to the thread capture chamber internal surface (64) to dispose the pair of hooks (66A)(66B) a distance apart at locations which allow corresponding engagement on opposed sides of the thread carrier (11), thereby flexing each of the pair of resiliently flexible hook members (65A)(65B) (as shown in the example of FIGS. 14C and 18B). Upon retraction of the thread carrier (11) from the thread capture chamber (16) the pair of resiliently flexible hook members (65A)(65B) each return toward the unflexed condition correspondingly disengaging each of the pair of hooks (66A)(66B) from the thread carrier (11).

Figure 5:
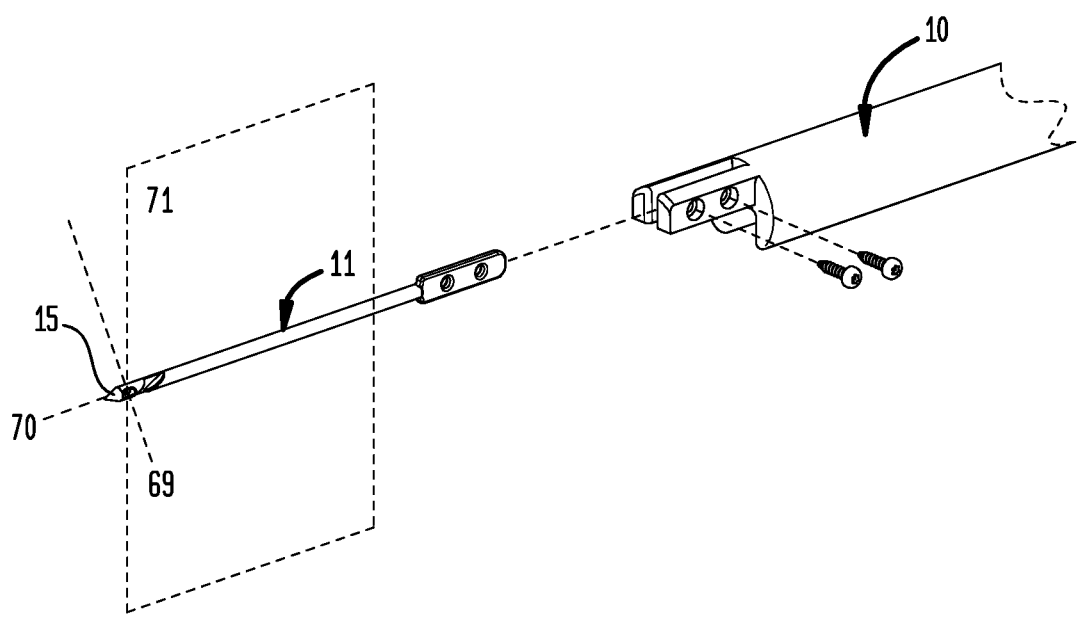
FIG. 5 is an exploded view of a particular embodiment of the thread carrier driver and thread carrier of the suturing apparatus shown in FIGS. 1 and 2.

Now referring primarily to FIGS. 3, 5, and 16, the thread carrier (11) can be coupled to the drive member first end (25) and extend axially outward to terminate in a thread carrier terminal end (15). The thread carrier (11) can comprise a slender rod which can, but need not necessarily, taper approaching the thread carrier terminal end (15). The taper can be sufficient to allow the thread carrier (11) to pass through a particular type of substrate (44), and as to particular embodiments the thread carrier (11) can taper to a sharp point at the thread carrier terminal end (15) to pass through a substrate (44) comprising animal tissue. A thread carrier aperture element (67) can be disposed a distance axially from said thread carrier terminal end (15). The aperture element (67) defines a thread carrier aperture (68). As to particular embodiments, the thread carrier aperture (68) can have a thread carrier aperture axis (69) disposed generally orthogonal to the thread carrier longitudinal axis (70) and generally orthogonal to the plane (71) longitudinally bisecting the chamber port (57) (as shown in the example of FIG. 13C).

Now referring primarily to FIGS. 5 and 16, the thread carrier (11) can further include a notch (72) disposed a distance axially from the thread carrier aperture element (67). The notch (72) defines a notch passage (73) between notch passage first and second ends (73A)(73B) which open on the thread carrier external surface. The notch (73) can be disposed angularly across the thread carrier longitudinal axis (70) of the thread carrier (11) to dispose the notch passage first end (73A) facing away from the chamber port (57) proximal the thread carrier terminal end (15) and the notch passage second end (73B) facing toward the chamber port (57) distal from the thread carrier terminal end (15). The hook (66A) or the pair of hooks (66A)(66B) engage the thread carrier (11) flexing at least one resiliently flexible hook member (65A) or pair of resiliently flexible hook members (65A)(65B) and aligning one of the hooks (66A) with the notch passage second end (73B). Resilient flexure moves the hook (66A) into the notch passage second end (73B). The hook (66A) travels through the notch passage (73) and disengages the thread carrier (11) by egress from the notch passage first end (73A).

Figure 21A:
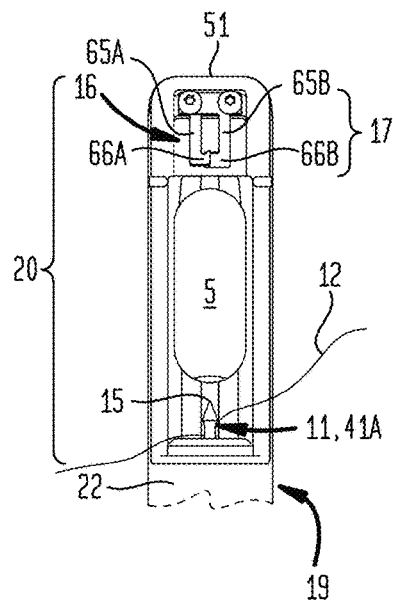
FIG. 21A is a top plan view of the suturing probe having the top portion removed to show the reciprocal movement of the thread carrier in a retracted condition.
Figure 21B:
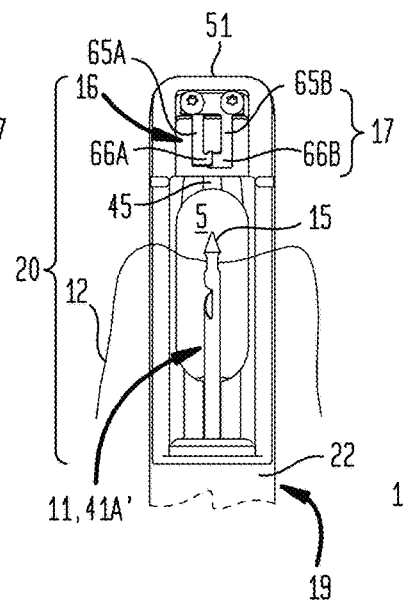
FIG. 21B is a top plan view of the suturing probe having the top portion removed to show the reciprocal movement of the thread carrier in an extended condition passing into the substrate capture chamber.
Figure 21C:
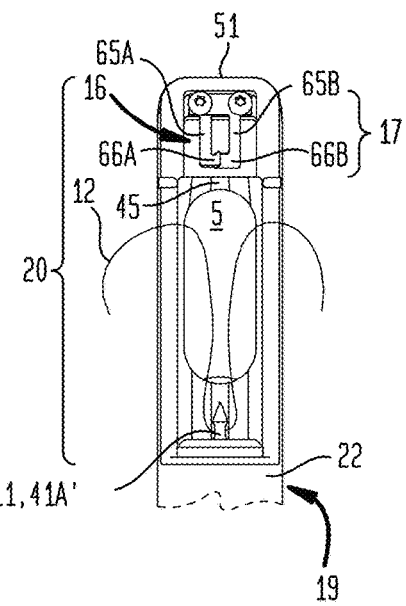
FIG. 21C is a top plan view of the suturing probe having the top portion removed to show the reciprocal movement of the thread carrier returned to the retracted condition outside of the substrate capture chamber.

Now referring primarily to FIGS. 21A through 21C, a thread (12) can be disposed in the thread carrier aperture element (67). As to particular embodiments, the thread carrier driver (10) can be operated bidirectionally to concurrently reciprocally position the thread carrier terminal end (15) between a thread carrier first position (41A) located outside of the substrate capture chamber (5) (as shown by the examples of FIGS. 21A and 21B) and a thread carrier second position (41A') with the thread carrier terminal end (15) located in the substrate capture chamber (5) as shown by (as shown by the example FIGS. 13C and 21C).

Now referring primarily to FIGS. 22A through 22C, as to particular embodiments, the thread carrier driver (10) can be operated to unidirectionally slidably engage a first tooth angled face (38A') of a first one of a pair of angled teeth (38A)(38B) with a peg (39) to dispose the peg (39) between the pair of angled teeth (38A)(38B) adjacent the first tooth base (38A") and to concurrently dispose the thread carrier terminal end (15) at a second position (41B) inside of the thread carrier conduit (45) or the thread capture chamber (16), thereby passing the thread (12) through the substrate (44) captured in the substrate capture chamber (5). Once the peg (39) traverses the first tooth angled face (38A') of the first one of the pair of teeth (38A)(38B), the resiliently flexible ratchet member (31) returns toward the unflexed position to dispose the peg (39) adjacent the first tooth base (38A') which prohibits the peg (39) from traveling toward the leading edge (36) of the resiliently flexible ratchet member (31) and prohibits the thread carrier (11) from being retracted from the thread carrier second position (41B) inside of the thread capture chamber (16).

Now referring primarily to FIGS. 23A through 23C, the thread carrier driver (10) can be operated to unidirectionally slidably engage the peg (39) with the second tooth angled face (38B') of the second one of the pair of teeth (38B) to concurrently engage the thread carrier terminal end (15) with the thread capture assembly (17).

Now referring primarily to FIGS. 14C, 18B, and 24A through 24C, continued operation of the thread carrier driver (10) unidirectionally slidably engages the peg (39) with the second one of the pair of teeth (38B) to dispose the peg (39) adjacent the second tooth base (38B") (as shown in the example of FIG. 14D) and concurrently engage the thread carrier terminal end (15) with the thread capture assembly (17) (as shown FIGS. 14C, 18B, and 24A through 24C) with the hook (66A) aligned with the notch passage second end (73B).

Now referring primarily to FIGS. 25A through 25C, once the peg (39) traverses the second one of the pair of angled teeth (38B) the resiliently flexible ratchet member (31) can return toward the unflexed position to dispose the peg (39) adjacent the second tooth base (38B"). The second tooth base (38B") can be beveled to allow the peg (39) to slidably engage the member second face (35) to travel toward the leading edge (36) of the resiliently flexible ratchet member (31), thereby retracting the thread carrier (11) from the thread capture assembly (17) and withdraw the substrate (44) captured in the substrate capture chamber (5). As the thread carrier (11) retracts, the hook (66A) aligned with the notch passage captures the thread (12) and retains the thread (12) on the hook (66A) (as shown in the example of FIGS. 24B and 25B), thereby disposing the thread (12) between the thread entry point (62A) and the thread withdrawal point (62B) (as shown in the example of FIG. 26).

As can be easily understood from the foregoing, the basic concepts of the present invention may be embodied in a variety of ways. The invention involves numerous and varied embodiments of a mountable carrier and methods for making and using such mountable carrier including the best mode.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "mount" should be understood to encompass disclosure of the act of "mounting"—whether explicitly discussed or not—and, conversely, were there effectively disclosure of the act of "mounting", such a disclosure should be understood to encompass disclosure of a "mount" and even a "means for mounting." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Thus, the applicant(s) should be understood to claim at least: i) each of the mountable carriers herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

I claim:

1. A thread capture device, comprising:
a thread carrier having a terminal end, said terminal end shaped as a sharpened point of a needle;
a notch disposed in said thread carrier proximate said thread carrier terminal end;
an aperture element having a pair of openings disposed on opposite sides of said thread carrier, said aperture element disposed between said thread carrier terminal end and said notch; and
a first resiliently flexible hook member terminating in a first hook, said thread carrier moves to slidably engage said first hook to pass into said notch disposed in said thread carrier.

2. The device of claim 1, wherein said notch defines a notch passage having a notch passage first end and a notch passage second end, wherein each of said notch passage first and second ends open on an external surface of said thread carrier.

3. The device of claim 2, wherein said notch passage disposed in angular relation to a longitudinal axis of said thread carrier.

4. The device of claim 2, wherein slidable engagement of said first hook with said thread carrier resiliently flexes said first resiliently flexible hook member, wherein resilient flexure of said resiliently flexible hook member moves said first hook into said notch passage.

5. The device of claim 4, wherein slidable engagement of said thread carrier with said first hook disposes a thread disposed in said aperture element adjacent said first resiliently flexible hook member prior to movement of said first hook through said notch passage, and passage of said first hook through said notch passage captures said thread with said first resiliently flexible hook member.

6. The device of claim 5, further comprising a second resiliently flexible hook member terminating in a second hook, said second resiliently flexible hook member disposed a distance from said first resiliently flexible hook member, said first hook overlapping said second hook, said thread carrier slidably engages said first hook and said second hook on opposite sides of said thread carrier.

7. The device of claim 1, wherein said thread carrier tapers approaching said thread carrier terminal end.

8. The device of claim 7, wherein said thread carrier tapers to a point approaching said thread carrier terminal end, said point capable of penetrating a substrate.

9. The device of claim 8, wherein said substrate comprises an animal tissue.

\* \* \* \* \*